(12) United States Patent
Hudson et al.

(10) Patent No.: US 7,192,582 B2
(45) Date of Patent: Mar. 20, 2007

(54) HUMAN MONOCLONAL ANTIBODIES TO FC ALPHA RECEPTOR (CD89)

(75) Inventors: Debra Hudson, Livermore, CA (US); Marcus A. van Dijk, Bilthoven (NL); Jan G. J. van de Winkel, Odijk (NL)

(73) Assignee: Medarex, Inc., Princeton, NJ (US)

( * ) Notice: Subject to any disclaimer, the term of this patent is extended or adjusted under 35 U.S.C. 154(b) by 230 days.

(21) Appl. No.: 10/073,644

(22) Filed: Feb. 11, 2002

(65) Prior Publication Data

US 2003/0082643 A1    May 1, 2003

Related U.S. Application Data

(60) Provisional application No. 60/338,956, filed on Nov. 5, 2001, provisional application No. 60/268,075, filed on Feb. 12, 2001.

(51) Int. Cl.
- A61K 39/40 (2006.01)
- A61K 39/42 (2006.01)
- C12N 5/00 (2006.01)
- C07K 16/00 (2006.01)
- C12P 21/08 (2006.01)

(52) U.S. Cl. ............ 424/139.1; 424/141.1; 424/142.1; 435/326; 435/346; 530/389.9; 530/388.15

(58) Field of Classification Search ........ 530/389.9, 530/388.15; 435/326, 346; 424/139.1, 141.1, 424/142.1
See application file for complete search history.

(56) References Cited

U.S. PATENT DOCUMENTS

| | | | |
|---|---|---|---|
| 5,198,342 A | 3/1993 | Maliszewski | 435/69.1 |
| 5,328,987 A | 7/1994 | Maliszewski | 530/350 |
| 5,610,057 A | 3/1997 | Shen et al. | 435/334 |
| 6,018,031 A * | 1/2000 | Shen et al. | 530/387.3 |
| 6,632,927 B2 * | 10/2003 | Adair et al. | 530/387.3 |

FOREIGN PATENT DOCUMENTS

| | | |
|---|---|---|
| CA | 2381565 A1 | 2/2001 |
| CA | 2408594 A1 | 11/2001 |
| EP | 496818 B1 | 6/1999 |
| WO | WO 92/03918 | 3/1992 |
| WO | WO 94/25585 | 11/1994 |
| WO | WO 98/02463 A1 | 1/1998 |
| WO | WO 98/24884 | 6/1998 |
| WO | WO 01/09186 A2 | 2/2001 |
| WO | WO 01/09186 A3 | 2/2001 |

OTHER PUBLICATIONS

Ngo et al., Protein Folding problem and Tertiary Structure prediction, 1994, Marz et al., (ed), Birkhauser, Boston, MA, pp. 433 and 492-495.*
Rudikoff et al. Proc Natl Acad Sci USA 1982 vol. 79 p. 1979.*
Panka et al., Proc Natl Acad Sci USA vol. 85 3080-3084 May 1988.*
Amit et al., Science vol. 233 747-753 1986.*
Monteiro, Renato C. et al. "Pathogenic significance of IgA receptor interactions in IgA nephropathy." *TRENDS in molecular Medicine* 8(10):464-8 (Oct. 2002).
Morgan, A. et al. "The N-terminal end of the $C_H^2$ domain of chimeric human IgG1 anti-HLA-DR is necessary for C1q, FcγRI and FcγRIII binding" *Immunology* 86:319-24 (1995).

* cited by examiner

*Primary Examiner*—Christina Chan
*Assistant Examiner*—Michail Belyavskyi
(74) *Attorney, Agent, or Firm*—Jane E. Remillard, Esquire; Lahive & Cockfield, LLP

(57) ABSTRACT

Human monoclonal antibodies which bind specifically to Fc alpha receptor (CD89), including monoclonal antibodies which react specifically to Fc receptor for IgA of human effector cells are disclosed. The binding agents, e.g., antibodies are useful for targeting human effector cells (e.g. macrophages) against a target cell (e.g. a cancer cell, an infectious agent, etc.). For this purpose, bifunctional antibodies or heteroantibodies can be constructed containing the binding region derived from an anti-Fc-alpha receptor antibody and the binding region of a target-specific antibody. Targeted effector cells can specifically lyse target cells.

16 Claims, 4 Drawing Sheets

Figure 1

Anti-CD89 14.1 VH

```
 Q   V   Q   L   V   E   S   G   G   G   V   V   Q   P   G   R   S   L
CAG GTG CAA CTG GTG GAG TCT GGG GGA GGC GTG GTC CAG CCT GGG AGG TCC CTG
                                                        CDR1
                                              ~~~~~~~~~~~~~~~~~~~~~~~~
 R   L   S   C   A   A   S   G   F   T   F   S   S   Y   V   L   H   W
AGA CTC TCC TGT GCA GCC TCT GGA TTC ACC TTC AGT AGT TAT GTT CTG CAC TGG
                                                                  CDR2
                                                            ~~~~~~~~~~~
 V   R   Q   A   P   G   K   G   L   D   W   V   A   V   I   S   D   D
GTC CGC CAG GCT CCA GGC AAG GGG CTG GAT TGG GTG GCA GTG ATA TCA GAT GAT
                  CDR2
~~~~~~~~~~~~~~~~~~~~~~~~~~~~~~~~~~~~~~~~~~~~~~~~~~~~
 G   R   N   K   Y   F   A   D   S   V   K   G   R   F   T   I   S   R
GGA AGG AAT AAA TAC TTC GCA GAC TCC GTG AAG GGC CGA TTC ACC ATC TCC AGA

D   N   S   K   N   T   L   Y   L   Q   M   N   S   L   R   A   E   D
GAC AAT TCC AAG AAC ACG CTG TAT CTG CAA ATG AAC AGC CTG AGA GCT GAG GAC
                                             CDR3
                                    ~~~~~~~~~~~~~~~~~~~~~~~~~~~~~~~~~~
 T   A   V   Y   Y   C   V   R   E   G   Y   S   G   S   W   F   D   Y
ACG GCT GTG TAT TAC TGT GTG AGA GAA GGG TAT AGC GGC AGC TGG TTT GAC TAC

W   G   Q   G   T   L   V   T   V   S   S
TGG GGC CAG GGA ACC CTG GTC ACC GTC TCC TCA
```

Figure 2

Anti-CD89 14.1 VK

```
 A   I   Q   L   T   Q   S   P   S   S   L   S   A   S   V   G   D   R
GCC ATC CAG TTG ACC CAG TCT CCA TCC TCC CTG TCT GCA TCT GTA GGA GAC AGA
                                             CDR1
                            ~~~~~~~~~~~~~~~~~~~~~~~~~~~~~~~~~~~~~~~~~~
 V   T   I   T   C   R   A   S   Q   G   I   S   S   A   L   A   W   Y
GTC ACC ATC ACT TGC CGG GCA AGT CAG GGC ATT AGC AGT GCT TTA GCC TGG TAT
                                                            CDR2
                                                    ~~~~~~~~~~~~~~~~~~
 Q   Q   K   P   G   K   A   P   K   L   L   I   Y   G   A   S   S   L
CAG CAG AAA CCA GGG AAA GCT CCT AAG CTC CTG ATC TAT GGT GCC TCC AGT TTG

CDR2
~~~~~~~~
 E   G   G   V   P   S   R   F   S   G   S   G   S   G   T   D   F   T
GAA GGT GGG GTC CCA TCA AGG TTC AGC GGC AGT GGA TCT GGG ACA GAT TTC ACT
                                                                CDR3
                                                            ~~~~~~~~~~
 L   T   I   S   S   L   Q   P   E   D   F   A   T   Y   Y   C   Q   Q
CTC ACC ATC AGC AGC CTG CAG CCT GAA GAT TTT GCA ACT TAT TAC TGT CAA CAG

CDR3
~~~~~~~~~~~~~~~~~~~~~~~~~~~~~~~
 F   N   S   Y   P   F   T   F   G   P   G   T   K   V   D   I   K
TTT AAT AGT TAC CCA TTC ACT TTC GGC CCT GGG ACC AAA GTG GAT ATC AAA
```

Figure 3

Anti-CD89 8.2 VH

```
 Q   V   Q   L   V   E   S   G   G   G   V   V   Q   P   G   R   S   L
CAG GTG CAG CTG GTG GAG TCT GGG GGA GGC GTG GTC CAG CCT GGG AGG TCC CTG
                                                          CDR1
                                                     ~~~~~~~~~~~~~~~~~~~
 R   L   S   C   A   A   S   G   F   T   F   S   S   Y   A   M   H   W
AGA CTC TCC TGT GCA GCC TCT GGA TTC ACC TTC AGT AGC TAT GCT ATG CAC TGG
                                                          CDR2
                                                     ~~~~~~~~~~~~~~~~~~~
 V   R   Q   A   P   G   K   G   L   E   W   V   A   V   I   S   Y   D
GTC CGC CAG GCT CCA GGC AAG GGG CTG GAG TGG GTG GCA GTT ATA TCA TAT GAT
                    CDR2
~~~~~~~~~~~~~~~~~~~~~~~~~~~~~~~~~~~~~~~~~~~~~~~~~~
 G   R   N   K   D   Y   A   D   S   V   K   G   R   F   T   I   S   R
GGA AGA AAT AAA GAC TAC GCA GAC TCC GTG AAG GGC CGA TTC ACC ATC TCC AGA

D   N   S   K   N   T   L   Y   L   Q   M   N   S   L   R   A   E   D
GAC AAT TCC AAG AAC ACG CTG TAT CTG CAA ATG AAC AGC CTG AGA GCT GAG GAC
                                                  CDR3
                                         ~~~~~~~~~~~~~~~~~~~~~~~~~~~~~~~
 T   A   V   H   Y   C   A   R   L   D   W   G   Y   D   A   F   D   I
ACG GCT GTG CAT TAC TGT GCG AGG CTT GAC TGG GGA TAT GAT GCT TTT GAT ATC

W   G   Q   G   T   M   V   T   V   S   S
TGG GGC CAA GGG ACA ATG GTC ACC GTC TCT TCA
```

Figure 4

Anti-CD89 8.2 VK

```
 E   I   V   L   T   Q   S   P   G   T   L   S   L   S   P   G   E   R
GAA ATT GTG TTG ACG CAG TCT CCA GGC ACC CTG TCT TTG TCT CCA GGG GAA AGA
                                        CDR1
                         ~~~~~~~~~~~~~~~~~~~~~~~~~~~~~~~~~~~~~~~~~~~~~~
 A   T   L   S   C   R   A   S   Q   S   V   S   S   S   Y   L   A   W
GCC ACC CTC TCC TGC AGG GCC AGT CAG AGT GTT AGC AGC AGC TAC TTA GCC TGG
                                                            CDR2
                                                ~~~~~~~~~~~~~~~~~~~~~~~
 Y   Q   Q   K   P   G   Q   A   P   R   L   L   I   Y   G   A   S   S
TAC CAG CAG AAG CCT GGC CAG GCT CCC AGG CTC CTC ATC TAT GGT GCA TCC AGC

CDR2
~~~~~~~~~~~~
 R   A   T   G   I   P   D   R   F   S   G   S   G   S   G   T   D   F
AGG GCC ACT GGC ATC CCA GAC AGG TTC AGT GGC AGT GGG TCT GGG ACA GAC TTC
                                                                    CDR3
                                                                    ~~~
 T   L   T   I   S   R   L   E   P   E   D   F   A   V   Y   Y   C   Q
ACT CTC ACC ATC AGC AGA CTG GAG CCT GAA GAT TTT GCA GTG TAT TAC TGT CAG

CDR3
~~~~~~~~~~~~~~~~~~~~~~~~~~~~~~~~~~~~~~
 Q   Y   G   S   S   P   P   Y   T   F   G   Q   G   T   K   L   E   I
CAG TAT GGT AGC TCA CCT CCG TAC ACT TTT GGC CAG GGG ACC AAG CTG GAG ATC

K
AAA
```

HUMAN MONOCLONAL ANTIBODIES TO FC ALPHA RECEPTOR (CD89)

RELATED APPLICATIONS

This application claims priority to U.S. Provisional Application No.: 60/268,075 filed on Feb. 12, 2001, and U.S. Provisional Application No.: 60/338,956 filed on Nov. 5, 2001, both of which are incorporated herein in their entirety by this reference.

BACKGROUND OF THE INVENTION

Receptors for the Fc portions of immunoglobulins are important in triggering many of the protective functions of monocytes, macrophages and polymorphonuclear cells. Receptors for IgG (Fcγ receptors or FcγR) on these cells have been extensively investigated and monoclonal antibodies against these receptors have been generated and shown to be therapeutically effective (See e.g. European Patent No. 255 249 entitled "Monoclonal Antibodies to Fc Receptor for Immunoglobulin G on Human Mononuclear Phagocytes").

IgA receptors (Fcα receptor or CD89) are also capable of promoting effector cell function. Binding of ligand to CD89 triggers phagocytosis and antibody mediated cell cytotoxicity in leukocytes and CD89-bearing cell lines. CD89 can also cooperate with receptors for IgG on effector cells in enhancing the phagocytosis of target cells.

CD89 is a receptor which binds to the Fc portion of IgA, the most abundant Ig in the human body (Kerr, M. A. 1990, *Biochem. J.* 271:285–296). CD89 is constitutively expressed primarily on cytotoxic immune effector cells including polymorphonuclear leukocytes (PMN), monocytes, macrophages, neutrophils and eosinophils. (Morton, H. C., et al., 1996 *Critical Reviews in Immunology* 16:423). CD89 expression on a sub-population of lymphocytes (Morton, H. C., et al., 1996 *Critical Reviews in Immunology* 16:423), and on glomerular mesangial cells also has been reported (Gomez-Guerrero, C., et al., 1996 *J. Immunol.* 156:4369–4376). Moreover, CD89 expression on monocytes and PMN can be enhanced by TNF-α (Gesl, A., et al., 1994 *Scad. J. Immunol.* 39:151–156; Hostoffer, R. W., et al., 1994, *The J. Infectious Diseases* 170:82–87), IL-1, GM-CSF, LPS or phorbol esters (Shen L., et al., *J. Immunol.* 152:4080–4086; Schiller, C. A. et al., 1994, *Immunology,* 81:598–604), whereas IFN-γ and TGF-β1 decrease FcαRI expression (Reterink, T. J. F., et al., 1996, *Clin. Exp. Immunol.* 103:161–166).

The α-chain of human CD89 is a heavily glycosylated, type one transmembrane molecule belonging to the Ig super-gene family which also includes receptors for IgG and IgE. One gene located on chromosome 19 encodes several alternatively spliced isoforms of the FcαRI alpha chain (55–110 kDa; Morton, H. C., et al., 1996 *Critical Reviews in Immunology* 16:423). Myelocytic CD89 has been shown to be associated with the FcR γ-chain which is implicated as playing a role in CD89 signal transduction (Morton, H. C. et al. 1995, *J. Biol. Chem.* 270:29781; Pfefferkorn, L. C., et al. 1995, *J. Immunol.,* 153:3228–3236, Saito, K. et al., 1995, *J. Allergy Clin. Immunol.* 96:1152).

CD89 binds both antigen-complexed and monomeric IgA1 and IgA2 (Mazangera, R. L. et al., 1990 *Biochem. J.* 272:159–165), consistent with the receptor being saturated in vivo with monomeric IgA in the same manner as FcγR and FcεRI are saturated with IgG and IgE respectively. Cross-linking CD89 on myeloid effector cells, by polymeric IgA, IgA immune complexes, or mAb specific for epitopes within or outside the ligand binding domain, stimulates degranulation, superoxide release, secretion of inflammatory cytokines, endocytosis and phagocytosis (Patty, C., A. Herbelin, A. Lihuen, J. F. Bach, and R. C. Monteiro. 1995 *Immunology.* 86:1–5; Stewart, W. W., R. L. Maz Yegera, L. Shen, and M. A. Kerr. 1994 *J. Leucocyte Biology.* 56:481–487; Stewart, W. W., and M. A. Kerr. 1990. *Immunology.* 71:328–334; Shen, L. 1992. *J. Leukocyte Biology.* 51:373–378.). These physiological responses triggered via CD89 can be important in the first line of humoral defense on mucosal surfaces (Morton, H. C., M. van Egmond, and J. G. J. van de Winkel. 1996 *Critical Reviews in Immunology.* 16:423).

SUMMARY OF THE INVENTION

The present invention provides improved immunotherapeutic agents for exploiting the therapeutic capacity of human CD89, a cytotoxic trigger molecule. In particular, the invention provides isolated human monoclonal antibodies which bind to human CD89, as well as therapeutic compositions, bispecific antibodies and molecular complexes containing such antibodies.

In a particular embodiment of the invention, the antibody is not inhibited by IgA, e.g., it binds to CD89 at a site different from the IgA binding site. In another embodiment, the antibody inhibits IgA binding to CD89, e.g., it binds to CD89 at a site which is within or near the IgA binding site.

In another particular embodiment of the invention, the antibody has the added benefit of not activating complement in vivo (e.g., not inducing complement mediated lysis of target cells) which reduces adverse side-effects during treatment. In still another embodiment, the antibody triggers at least one Fc receptor-mediated effector cell activity, such as phagocytosis or secretion of superoxide anion.

In another particular embodiment of the invention, the antibody is an IgG1 (e.g., IgG1k) antibody, e.g., having an IgG1 heavy chain and a kappa light chain. Other antibody isotypes also encompassed by the invention include IgG2, IgG3, IgG4, IgM, IgA1, IgA2, IgAsec, IgD, and IgE. The antibodies can be whole antibodies or antigen-binding fragments of the antibodies, including Fab, F(ab')$_2$, Fv and chain Fv fragments.

In another particular embodiment of the invention, the antibody is encoded by human IgG heavy chain and human kappa light chain nucleic acids comprising nucleotide sequences in their variable regions as set forth in SEQ ID NOs: 1 or 5 and SEQ ID NOs: 3 or 7, respectively, and conservative sequence modifications thereof. In another embodiment, the human antibody includes IgG heavy chain and kappa light chain variable regions which comprise the amino acid sequences shown in SEQ ID NOs: 2 or 6 and SEQ ID NOs: 4 or 8, respectively, and conservative sequence modifications thereof.

Particular antibodies of the present invention include, for example, human monoclonal antibodies (mAbs) 14.1, 7.4, and 8.2 (also referred to as 14A8, 7F12, and 8D2, respectively), or an antibody that binds to the same epitope as (e.g., competes with) or has the same functional binding characteristics as antibody 14.1, 7.4 or 8.2.

Human antibodies of the invention can be produced recombinantly in a host cell (e.g., a CHO cell or a lymphocytic cell) or be obtained directly from a hybridoma which expresses the antibody (i.e., which includes a B cell obtained from a transgenic non-human animal, e.g., a transgenic mouse, having a genome comprising a human heavy chain transgene and a human light chain transgene that encode the antibody, fused to an immortalized cell).

In another particular embodiment of the invention, the human antibody of the present invention can be characterized by one or more of the following properties:

(a) binding specificity for human CD89;

(b) a binding equilibrium association constant (Ka) to human CD89 of at least about $10^7$ M$^{-1}$;

(c) a dissociation constant (Kd) from human CD89 of about $10^{-8}$ S$^{-1}$ or less;

(c) absence of complement activation upon in vivo binding to CD89;

(d) binding to human CD89 at a site which does not inhibit human IgA binding;

(e) a heavy chain comprising the amino acid sequence shown in SEQ ID NOs: 2 or 6 and conservative sequence modifications thereof, and a light chain comprising the amino acid sequence shown in SEQ ID NOs: 4 or 8 and conservative sequence modifications thereof.

In another aspect, the present invention provides nucleic acid molecules encoding the human monoclonal antibodies, or antigen-binding portions thereof. Recombinant expression vectors which include nucleic acids encoding antibodies of the invention, and host cells transfected with such vectors, are also encompassed by the invention, as are methods of making the antibodies of the invention by culturing such host cells, e.g., an expression vector comprising a nucleotide sequence encoding the variable and constant regions of the heavy and light chains of mAbs 14.1, 7.4 or 8.2.

In yet another aspect, the invention provides isolated B-cells from a transgenic non-human animal, e.g., a transgenic mouse, which express human anti-CD89 antibodies of the invention. Preferably, the isolated B cells are obtained from a transgenic non-human animal, e.g., a transgenic mouse, which has been immunized with a purified or enriched preparation of CD89 antigen and/or cells expressing CD89. Preferably, the transgenic non-human animal, e.g., a transgenic mouse, has a genome comprising a human heavy chain transgene and a human light chain transgene encoding all or a portion of an antibody of the invention. The isolated B-cells are then immortalized to provide a source (e.g., a hybridoma) of human anti-CD89 antibodies.

Accordingly, the present invention also provides a hybridoma capable of producing human monoclonal antibodies of the invention that specifically bind to CD89. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell. Particular hybridomas of the invention include 14.1, 7.4, and 8.2.

In yet another aspect, the invention provides a transgenic non-human animal, such as a transgenic mouse (also referred to herein as a "HuMab"), which express human monoclonal antibodies that specifically bind to CD89. In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of CD89 antigen and/or cells expressing CD89. Preferably, the transgenic non-human animal, e.g., the transgenic mouse, is capable of producing multiple isotypes of human monoclonal antibodies to CD89 (e.g., IgG, IgA and/or IgM) by undergoing V-D-J recombination and isotype switching. Isotype switching may occur by, e.g., classical or non-classical isotype switching.

In another aspect, the present invention provides methods for producing human monoclonal antibodies which specifically react with CD89. In one embodiment, the method includes immunizing a transgenic non-human animal, e.g., a transgenic mouse, having a genome comprising a human heavy chain transgene and a human light chain transgene encoding all or a portion of an antibody of the invention, with a purified or enriched preparation of CD89 antigen and/or cells expressing CD89. B cells (e.g., splenic B cells) of the animal are then obtained and fused with myeloma cells to form immortal, hybridoma cells that secrete human monoclonal antibodies against CD89.

In yet another aspect, human anti-CD89 antibodies of the invention are derivatized, linked to or co-expressed with another functional molecule, e.g., another peptide or protein (e.g., antibody or antibody fragment, such as an Fab' fragment). For example, an antibody or antigen-binding portion of the invention can be functionally linked (e.g., by chemical coupling, genetic fusion, noncovalent association or otherwise) to one or more other molecular entities, such as another antibody (e.g., to produce a bispecific or a multispecific antibody), a cytoxin, a cellular ligand or an antigen. Bispecific and multispecific antibodies of the present invention are useful for targeting a cell expressing CD89, e.g., an effector cell, to a selected antigen, such as an epitope on a tumor cell, an autoantibody producing cell, a pathogen infected cell, or any other undesirable cell, thereby resulting in cytolysis or phagocytosis of the cell or pathogen associated with the antigen. Other target antigens include soluble antigens or complexes of antigens and microorganisms, e.g., viruses, parasites, and bacteria.

Multispecific molecules of the invention also include trispecific, tetraspecific and other multispecific molecules. In one embodiment the multispecific molecule includes an anti-enhancement factor (EF) portion, e.g., a molecule which binds to a surface protein involved in cytotoxic activity.

Accordingly, present invention encompasses a large variety of antibody conjugates, bi- and multispecific molecules, and fusion proteins, all of which bind to CD89 expressing cells and which target other molecules to the cells, or which bind to CD89 and to other molecules or cells.

In another aspect, the present invention provides a conjugate comprising a human anti-CD89 antibody of the invention linked to a therapeutic moiety, e.g., a cytotoxic drug, an enzymatically active toxin, or a fragment thereof, a radioisotope, or a small molecule anti-cancer drug.

Alternatively, human antibodies of the invention can be co-administered with such therapeutic and cytotoxic agents, but not linked to them. They can be coadministered simultaneously with such agents (e.g., in a single composition or separately) or can be administered before or after administration of such agents. Such agents can include cytokines, such as G-CSF, GM-CSF, IL-2 or IFN-alpha, and chemotherapeutic agents such as doxorubicin (adriarnycin), cisplatin bleomycin sulfate, carmustine, chlorambucil, and cyclophosphamide hydroxyurea. Human antibodies of the invention also can be administered in conjunction with radiation therapy.

In another aspect, the present invention provides compositions, e.g., pharmaceutical and diagnostic compositions/kits, comprising a pharmaceutically acceptable carrier and at least one human monoclonal antibody of the invention, or an antigen-binding portion thereof, which specifically binds to CD89. In one embodiment, the composition comprises a combination of the human antibodies or antigen-binding portions thereof, preferably each of which binds to a distinct epitope. Compositions, e.g., pharmaceutical compositions, comprising a combination of at least one human monoclonal antibody of the invention, or antigen-binding portions thereof, and at least one bispecific or multispecific molecule of the invention, are also within the scope of the invention.

For use in in vivo treatment and prevention of diseases related to CD89 expression (e.g., over-expression), human antibodies of the invention are administered to patients (e.g., human subjects) at therapeutically effective dosages using any suitable route of administration, such as injection and other routes of administration known in the art for antibody-based clinical products.

Human antibodies of the present invention can also be used to modulate CD89 levels on effector cells such as by capping and elimination of receptors on the cell surface. Mixtures of anti-Fc receptors can also be used for this purpose.

In another embodiment, human antibodies of the present invention which block or inhibit IgA binding to CD89 are useful in the treatment of diseases characterized by circulating IgA-containing complexes and/or precipitation of IgA-immune complexes, e.g., chronic hepatitis, Henoch-Schonlein purpura (HSP), IgA nephropathy (Berger's disease), or IgA-glomerulonephritis. A human antibody of the invention can be administered to a patient suffering from such a disease to inhibit or downregulate the binding of endogenous IgA to CD89 in vivo.

Based on their ability to bind both CD89 bearing immune cells and specific target cells (i.e., cells whose elimination would be beneficial for the host), bispecific and multispecific molecules of the present can be used in the treatment of a wide variety of diseases. Such diseases include, but are not limited to, autoimmune diseases and cancers (e.g., bladder, breast, colon, kidney, ovarian, testicular, prostate, lung, brain, rectum, pancreas, liver, central nervous system, head and neck, kidney, bone, blood, and lymphatic system), pathogenic infections such as viral (e.g., HIV, HTLV, and FELV), protozoan (e.g., *Toxoplasma gondii*), fungal (e.g., *Candida albicans*), and bacterial (e.g., *Staphylococcus aureus, Streptococcus hemolyticus*, and *Mycobacterium tuberculsis*). Another aspect of the invention provides molecules that are useful for vaccination against diseases and cancer by including an antigen from disease organisms, from infected cells, from gene products of disease organisms or from cancer cells. For these purposes, the invention provides compositions which are binding agents that link the useful operative antigen to a binding determinant that directs the antigen to the immune system.

In one embodiment, the patient is additionally treated with a chemotherapeutic agent, radiation, or an agent that modulates, e.g., enhances or inhibits, the expression or activity of an Fc receptor, e.g., an Fcα receptor or an Fcγ receptor, such as a cytokine. Typical cytokines for administration during treatment include granulocyte colony-stimulating factor (G-CSF), granulocyte-macrophage colony-stimulating factor (GM-CSF), interferon-γ (IFN-γ), and tumor necrosis factor (TNF). Typical therapeutic agents include, among others, anti-neoplastic agents such as doxorubicin (adriamycin), cisplatin bleomycin sulfate, carmustine, chlorambucil, and cyclophosphamide hydroxyurea.

In yet another aspect, the present invention provides a method for detecting in vitro or in vivo the presence of CD89 in a sample, e.g., for diagnosing a CD89-related disease. In one embodiment, this is achieved by contacting a sample to be tested, optionally along with a control sample, with a human monoclonal antibody of the invention (or an antigen-binding portion thereof) under conditions that allow for formation of a complex between the antibody and CD89. Complex formation is then detected (e.g., using an ELISA). When using a control sample along with the test sample, complex is detected in both samples and any statistically significant difference in the formation of complexes between the samples is indicative the presence of CD89 in the test sample.

Other features and advantages of the instant invention be apparent from the following detailed description and examples which should not be construed as limiting. The contents of all references, patents and published patent applications cited throughout this application are expressly incorporated herein by reference.

BRIEF DESCRIPTION OF THE DRAWINGS

FIG. 1 shows the nucleotide sequence (SEQ ID NO:1) and corresponding amino acid sequence (SEQ ID NO:2) of the $V_H$-region from HuMAb 14.1. CDR regions are also delineated. The germline segments utilized for the HuMAb 14.1 $V_H$-region include $V_H$ 3-30.3 (SEQ ID NO:9), D 6–13 (SEQ ID NO:12), and JH4b (SEQ ID NO:13).

FIG. 2 shows the nucleotide sequence (SEQ ID NO:3) and corresponding amino acid sequence (SEQ ID NO:4) of the $V_K$-region from HuMAb 14.1. CDR regions are also delineated. The germline segments utilized for the HuMAb 14.1 $V_K$-region include $V_K$ L18 (SEQ ID NQ:10) and JK3 (SEQ ID NO:14).

FIG. 3 shows the nucleotide sequence (SEQ ID NO:5) and corresponding amino acid sequence (SEQ ID NO:6) of the $V_H$-region from HuMAb 8D2. CDR regions are also delineated. The germline segments utilized for the HuMAb 8D2 $V_H$-region include $V_H$ 3–30.3 (SEQ ID NO:9), D 7–27 (SEQ ID NO:15), and JH3b (SEQ ID NQ:16).

FIG. 4 shows the nucleotide sequence (SEQ ID NO:7) and corresponding amino acid sequence (SEQ ID NO:8) of the $V_K$-region from HuMAb 8D2. CDR regions are also delineated. The germline segments utilized for the HuMAb 8D2 $V_K$-region include $V_K$ A27 (SEQ ID NO:11) and JK2 (SEQ ID NO:17).

DETAILED DESCRIPTION OF THE INVENTION

The present invention provides isolated human monoclonal antibodies, including antigen-binding portions thereof, which bind to an epitope present on a human IgA receptor (CD89). In one embodiment, the human antibodies are produced in a non-human transgenic animal, e.g., a transgenic mouse, capable of producing multiple isotypes of human monoclonal antibodies to CD89 (e.g., IgG, IgA and/or IgE) by undergoing V-D-J recombination and isotype switching. Accordingly, particular aspects of the invention include not only antibodies, antibody fragments, and pharmaceutical compositions thereof, but also non-human transgenic animals, B-cells and hybridomas which produce monoclonal antibodies. Methods of using the antibodies of the invention to detect a cell expressing CD89 or to trigger effector functions in a cell expressing CD89 (for example by crosslinking CD89 molecules using a bispecific antibody comprising an anti-CD89 antibody of the invention and another antibody directed against an antigen on a target cell), either in vitro or in vivo, are also encompassed by the invention. Methods of using the antibodies of the invention to block or inhibit IgA binding to CD89 are also provided and are useful in the treatment of diseases characterized by abnormal endogenous IgA, such as diseases characterized by circulating IgA-containing complexes and/or precipitation of IgA-immune complexes, e.g., chronic hepatitis, Henoch-Schonlein purpura (HSP), IgA nephropathy (Berger's disease), or IgA-glomerulonephritis.

In order that the present invention may be more readily understood, certain terms are first defined. Additional definitions are set forth throughout the detailed description.

As used herein, the terms "CD89," "human IgA receptor," and "Fc-alpha receptor" (FcαRI) are used interchangeably and are intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) Critical Reviews in Immunology 16:423–440). FcαRI receptors are preferred trigger receptors for use in the invention because they are (1) expressed primarily on immune effector cells, e.g., monocytes, macrophages, neutrophils and eosinophils; (2) expressed at high levels (e.g., 5,000–100,000 per cell); (3) mediators of cytotoxic activities (e.g., ADCC, phagocytosis); (4) mediate enhanced antigen presentation of antigens, including self-antigens, targeted to them.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcαRI has been found to be up-regulated by G-CSF or GM-CSF. This enhanced expression increases the effector function of FcαRI-bearing cells against targets. An effector cell can phagocytose or lyse a target antigen or a target cell.

"Target cell" shall mean any undesirable cell in a subject (e.g., a human or animal) that can be targeted by a composition (e.g., a human monoclonal antibody, a bispecific, or a multispecific molecule) of the invention. In one embodiment, the target cell is a cell expressing or overexpressing CD89. In another embodiment, target cells include tumor cells. Tumor cells that can be targeted are tumor cells of any type of cancer, including cancer of breast, ovarian, prostate, testicular, lung, colon, rectum, pancreas, liver, central nervous system, kidney, head, neck, bone, blood, and lymphatic system. In addition to tumor cells, the effector cell can be targeted against auto-antibody producing lymphocytes for treatment of autoimmune disease or an IgE-producing lymphocyte for treatment of allergy. The target can also be microorganism (bacterium or virus) or a soluble antigen (such as rheumatoid factor, or other auto-antibodies and toxins). A microorganism is intended to include pathogens, e.g., viruses, bacteria, fungi, protozoa.

The term "antigen" means any natural or synthetic immunogenic substance, a fragment or portion of an immunogenic substance, a peptide epitope, or a hapten. The term "antigen" also includes substances which are nonimmunogenic in uncomplexed form, but are immunogenic when complexed. The term "uncomplexed" includes substances which are not linked to form a molecular complex of the present invention. The term "complexed" includes substances which are linked to form a molecular complex of the present invention.

As used herein, the term "inhibits growth" (e.g., referring to cells) is intended to include any measurable decrease in the growth of a cell when contacted with an anti-CD89 antibody as compared to the growth of the same cell not in contact with an anti-CD89 antibody, e.g., the inhibition of growth of a cell by at least about 10%, 20%, 30%, 40%, 50%, 60%, 70%, 80%, 90%, 99%, or 100%.

As used herein, the terms "inhibits binding" and "blocks binding" (e.g., referring to inhibition/blocking of binding of CD89 ligand, e.g., IgA, to CD89) are used interchangeably and encompass both partial and complete inhibition/blocking. The inhibition/blocking of IgA to CD89 preferably reduces or alters the normal level or type of effector cell functions that occurs when IgA binds to CD89 without inhibition or blocking. Inhibition and blocking are also intended to include any measurable decrease in the binding affinity of IgA to CD89 when in contact with an anti-CD89 antibody as compared to the ligand not in contact with an anti-CD89 antibody, e.g., the blocking of CD89 ligands to CD89 by at least about 10%, 20%, 30%, 40%, 50%, 60%, 70%, 80%, 90%, 99%, or 100%.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., CD89). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell, e.g., CD89. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fe receptor on the surface of an effector cell, and (c) at least one other component. Accordingly, the invention includes, but is not limited to, bispecific, trispecific, tetraspecific, and other multispecific molecules which are directed to cell surface antigens, such as CD89, and to other targets, such as Fc receptors on effector cells.

The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444–6448; Poljak, R. J., et al. (1994) *Structure* 2:1121–1123).

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, is intended to include all human antibodies that are prepared, expressed, created or isolated by recombinant means, such as (a) antibodies isolated from an animal (e.g., a mouse) that is transgenic for human immunoglobulin genes (described further in Section I, below), (b) antibodies expressed using a recombinant expression vector transfected into a host cell, (c) antibodies isolated from a recombinant, combinatorial human antibody library, and (c) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

An "isolated antibody," as used herein, is intended to refer to an antibody which is substantially free of other antibodies having different antigenic specificities (e.g., an isolated antibody that specifically binds to CD89 is substantially free of antibodies that specifically bind antigens other than CD89). An isolated antibody that specifically binds to an epitope, isoform or variant of human CD89 may, however, have cross-reactivity to other related antigens, e.g., from other species (e.g., CD89 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity of at least about $1\times10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to a binding affinity of at least about $10^7 M^{-1}$, preferably at least about $10^8 M^{-1}$, more preferably at least about $10^9 M^{-1}$, $10^{10} M^{-1}$, $10^{11} M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $1\times10^7 M^{-1}$.

The term "$K_{assoc}$" or "$K_a$" as used herein, is intended to refer to the association constant of a particular antibody-antigen interaction.

The term "$K_{dis}$" or "$K_d$", as used herein, is intended to refer to the dissociation constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first $C_H$ gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ϵ, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the non-human transgenic animal than to the species from which the $C_H$ genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., VH, VL, CDR3) that bind to CD89, is intended to refer to a nucleic acid molecule in which the nucleotide sequences encoding the antibody or antibody portion are free of other nucleotide sequences encoding antibodies or antibody portions that bind antigens other than CD89, which other sequences may naturally flank the nucleic acid in human genomic DNA. In one embodiment, the human anti-CD89 antibody, or portion thereof, includes the nucleotide or amino acid sequence of 14.1, 7.4, 8.2, as well as heavy chain (VH) and light chain (VL) variable regions having the sequences shown in SEQ ID NOs: 1, 3, 5, 7, and 2, 4, 6, 8, respectively.

As disclosed and claimed herein, the sequences set forth in SEQ ID NOs: 1–8 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1–8 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD89 antibody is preferably replaced with another amino acid residue from the same side chain family.

Alternatively, in another embodiment, mutations can be introduced randomly along all or part of a anti-CD89 antibody coding sequence, such as by saturation mutagenesis, and the resulting modified anti-CD89 antibodies can be screened for binding activity.

Accordingly, antibodies encoded by the (heavy and light chain variable region) nucleotide sequences disclosed herein (i.e., SEQ ID NOs: 1, 3, 5, and 7) and/or containing the (heavy and light chain variable region) amino acid sequences disclosed herein (i.e., SEQ ID NOs: 2, 4, 6, and 8) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs: 1–8 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11–17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444–453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

Various aspects of the invention are described in further detail in the following subsections.

I. Production of Human Antibodies to CD89

The monoclonal antibodies (mAbs) of the invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against CD89 can be generated using transgenic mice carrying parts of the human immune system rather than the mouse system. These transgenic mice, referred to herein as "HuMab" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, et al. (1994) *Nature* 368(6474): 856–859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49–101; Lonberg, N. and Huszar, D. (1995) *Intern. Rev. Immunol.* Vol. 13: 65–93, and Harding, F. and Lonberg, N. (1995) *Ann. N.Y. Acad. Sci* 764: 536–546). The preparation of HuMab mice is described in detail Section II below and in Taylor, L. et al. (1992) *Nucleic Acids Research* 20:6287–6295; Chen, J. et al. (1993) *International Immunology* 5: 647–656; Tuaillon et al. (1993) *Proc. Natl. Acad. Sci USA* 90:3720–3724; Choi et al. (1993) *Nature Genetics* 4:117–123; Chen, J. et al. (1993) *EMBO J.* 12: 821–830; Tuaillon et al. (1994) *J. Immunol.* 152:2912–2920; Lonberg et al., (1994) *Nature* 368(6474): 856–859; Lonberg, N. (1994) *Handbook of Experimental Pharmacology* 113:49–101; Taylor, L. et al. (1994) *International Immunology* 6: 579–591; Lonberg, N. and Huszar, D. (1995) *Intern. Rev. Immunol.* Vol. 13: 65–93; Harding, F. and Lonberg, N. (1995) *Ann. N.Y. Acad. Sci* 764:536–546; Fishwild, D. et al. (1996) *Nature Biotechnology* 14: 845–851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity. Alternatively, the HCO12 transgenic mice described in Example 2, can be used to generate human anti-CD89 antibodies.

HuMab Immunizations

To generate fully human monoclonal antibodies to CD89, HuMab mice can be immunized with a purified or enriched preparation of CD89 antigen and/or cells expressing CD89, as described by Lonberg, N. et al. (1994) *Nature* 368(6474): 856–859; Fishwild, D. et al. (1996) *Nature Biotechnology* 14: 845–851 and WO 98/24884. Preferably, the mice will be 6–16 weeks of age upon the first infusion. For example, a purified or enriched preparation (5–20 μg) of CD89 antigen (e.g., purified from CD89-expressing LNCaP cells) can be used to immunize the HuMab mice intraperitoneally. In the event that immunizations using a purified or enriched preparation of CD89 antigen do not result in antibodies, mice can also be immunized with cells expressing CD89, e.g., a tumor cell line, to promote immune responses.

Cumulative experience with various antigens has shown that the HuMab transgenic mice respond best when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-CD89 human immunoglobulin can be used for fusions. Mice can be boosted intravenously with antigen 3 days before sacrifice and removal of the spleen. It is expected that 2–3 fusions for each antigen may need to be performed. Several mice will be immunized for each antigen. For example, a total of twelve HuMab mice of the HC07 and HC012 strains can be immunized.

Generation of Hybridomas Producing Human Monoclonal Antibodies to CD89

The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM L~glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells are cultured in medium in which the HAT is replaced with HT. Individual wells are then screened by ELISA for human anti-CD89 monoclonal IgM and IgG antibodies. Once extensive hybridoma growth occurs, medium is observed usually after 10–14 days. The antibody secreting hybridomas are replated, screened again, and if still positive for human IgG, anti-CD89 monoclonal antibodies, can be subcloned at least twice by limiting dilution. The stable subclones are then cultured in vitro to generate small amounts of antibody in tissue culture medium for characterization.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323–327; Jones, P. et al., 1986, *Nature* 321:522–525; and Queen, C. et al., 1989, *Proc. Natl. Acad. See*. U.S.A. 86:10029–10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences cab be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, *J. Biol. Chem.* 266L19867019870); and, HindIII sites are engineered upstream of the translation initiation sites.

For both the heavy and light chain variable regions, the optimized coding, and corresponding non-coding, strand sequences are broken down into 30–50 nucleotide approximately the midpoint of the corresponding non-coding oligonucleotide. Thus, for each chain, the oligonucleotides can be assemble into overlapping double stranded sets that span segments of 150–400 nucleotides. The pools are then used as templates to produce PCR amplification products of 150–400 nucleotides. Typically, a single variable region oligonucleotide set will be broken down into two pools which are separately amplified to generate two overlapping PCV products. These overlapping products are then combined by PCT amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric $IgG_1\kappa$ or $IgG_4\kappa$ antibodies. Similar plasmids can be constructed for expression of other heavy chain isotypes, or for expression of antibodies comprising lambda light chains.

Thus, in another aspect of the invention, the structural features of an human anti-CD89 antibodies of the invention, 14.1, 7.4, or 8.2, are used to create structurally related human anti-CD89 antibodies that retain at least one functional property of the antibodies of the invention, such as binding to CD89. More specifically, one or more CDR regions of 14.1, 7.4, or 8.2 can be combined recombinantly with known human framework regions and CDRs to create additional, recombinantly-engineered, human anti-CD89 antibodies of the invention.

Accordingly, in another embodiment, the invention provides a method for preparing an anti-CD89 antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIG. 1 or 3 (or corresponding amino acid residues in SEQ ID NOs: 2 or 6); and (2) human light chain framework regions and human light chain CDRs, wherein at least one of the human light chain CDRs comprises an amino acid sequence selected from the amino acid sequences of CDRs shown in FIG. 2 or 4 (or corresponding amino acid residues in SEQ ID NOs: 4 or 8);

wherein the antibody retains the ability to bind to CD89.

The ability of the antibody to bind CD89 can be determined using standard binding assays, such as those set forth in the Examples (e.g., an ELISA).

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of 14.1, 7.4, or 8.2. The antibodies further can comprise the CDR2s of 14.1, 7.4, or 8.2. The antibodies further can comprise the CDR1s of 14.1, 7.4, or 8.2. Accordingly, the invention further provides anti-CD89 antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of 14.1, 7.4, and 8.2 as shown in FIG. 1 or 3 (or corresponding amino acid residues in SEQ ID NOs: 2 or 6); and (2) human light chain framework regions, a human light chain CDR1 region, a human light chain CDR2 region, and a human light chain CDR3 region, wherein the human light chain CDR3 region is selected from the CDR3s of 14.1, 7.4, and 8.2 as shown in FIGS. 2 and 4 (or corresponding amino acid residues in SEQ ID NOs: 4 or 8), wherein the antibody binds CD89. The antibody may further comprise the heavy chain CDR2 and/or the light chain CDR2 of 14.1, 7.4, or 8.2. The antibody may further comprise the heavy chain CDR1 and/or the light chain CDR1 of 14.1, 7.4, or 8.2.

Preferably, the CDR1, 2, and/or 3 of the engineered antibodies described above comprise the exact amino acid sequence(s) as those of 14.1, 7.4, or 8.2 disclosed herein. However, the ordinarily skilled artisan will appreciate that some deviation from the exact CDR sequences of 14.1, 7.4, and 8.2 may be possible while still retaining the ability of the antibody to bind CD89 effectively (e.g., conservative substitutions). Accordingly, in another embodiment, the engineered antibody may be composed of one or more CDRs that are, for example, 90%, 95%, 98% or 99.5% identical to one or more CDRs of 14.1, 7.4, or 8.2.

In addition to simply binding CD89, engineered antibodies such as those described above may be selected for their retention of other functional properties of antibodies of the invention, such as:

1) binding to live cells expressing CD89;
2) high affinity binding to CD89;
3) binding to a unique epitope on CD89 (to eliminate the possibility that monoclonal antibodies with complimentary activities when used in combination would compete for binding to the same epitope;
4) opsonization of cells expressing CD89; and/or
5) mediation of growth inhibition, phagocytosis and/or killing of cells expressing CD89 in the presence of human effector cells.

Characterization of Binding of Human Monoclonal Antibodies to CD89

To characterize binding of human monoclonal CD89 antibodies of the invention, sera from immunized mice can be tested, for example, by ELISA. In a typical (but non-limiting) example of an ELISA protocol, microtiter plates are coated with purified CD89 at 0.25 µg/ml in PBS, and then blocked with 5% bovine serum albumin in PBS. Dilutions of plasma from CD89-immunized mice are added to each well and incubated for 1–2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at OD of 405–650. Preferably, mice which develop the highest titers will be used for fusions.

An ELISA assay as described above can also be used to screen for hybridomas that show positive reactivity with CD89 immunogen. Hybridomas that bind with high avidity to CD89 will be subcloned and further characterized. One clone from each hybridoma, which retains the reactivity of the parent cells (by ELISA), can be chosen for making a 5–10 vial cell bank stored at −140° C., and for antibody purification.

To purify human anti-CD89 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-CD89 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD89 coated-ELISA plates as described above. Biotinylated mAb binding can be detected with a strep-avidin-alkaline phosphatase probe.

To determine the isotype of purified antibodies, isotype ELISAs can be performed. For example, wells of microtiter plates can be coated with 10 µg/ml of anti-human Ig overnight at 4° C. After blocking with 5% BSA, the plates are reacted with 10 µg/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

In order to demonstrate binding of monoclonal antibodies to live cells expressing the CD89, flow cytometry can be used. In a typical (but non-limiting) example of a flow cytometry protocol, cell lines expressing CD89 (grown under standard growth conditions) are mixed with various concentrations of monoclonal antibodies in PBS containing 0.1% Tween 80 and 20% mouse serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD89 human IgGs can be further tested for reactivity with CD89 antigen by Western blotting. For example, cell extracts from cells expressing CD89 can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

II. Production of Transgenic Nonhuman Animals Which Generate Human Monoclonal Anti-CD89 Antibodies In yet another aspect, the invention provides transgenic non-human animals, e.g., a transgenic mice, which are capable of expressing human monoclonal antibodies that specifically bind to CD89, preferably with high affinity. In a preferred embodiment, the transgenic non-human animals, e.g., the transgenic mice (HuMab mice), have a genome comprising a human heavy chain transgene and a light chain transgene. In one embodiment, the transgenic non-human animals, e.g., the transgenic mice, have been immunized with a purified or enriched preparation of CD89 antigen and/or cells expressing CD89. Preferably, the transgenic non-human animals, e.g., the transgenic mice, are capable of producing multiple isotypes of human monoclonal antibodies to CD89 (e.g., IgG, IgA and/or IgE) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire, requires that the heterologous immunoglobulin transgenes contain within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y., which is incorporated herein by reference.

In certain embodiments, the transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305–7316 (1991); Sideras et al., *Intl. Immunol.* 1:631–642 (1989), which are incorporated herein by reference).

For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to CD89 antigen.

In an alternate embodiment, the transgenes comprise an unrearranged "mini-locus." Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic animal used to generate human antibodies to CD89 contains at least one, typically 2–10, and sometimes 25–50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10: 1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., staphylococcus protein A. Typically, the immunoglobulins will exhibit an affinity for preselected antigens of at least about $10^7 M^{-1}$, preferably at least about $10^9 M^{-1}$, more preferably at least about $10^{10} M^{-1}$, $10^{11} M^{-1}$, $10^{12} M^{-1}$, or greater, e.g., up to $10^{13} M^{-1}$ or greater.

In some embodiments, it may be preferable to generate mice with predetermined repertoires to limit the selection of V genes represented in the antibody response to a predetermined antigen type. A heavy chain transgene having a predetermined repertoire may comprise, for example, human VH genes which are preferentially used in antibody responses to the predetermined antigen type in humans. Alternatively, some VH genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g. by hybridization or DNA sequencing, as being from a species of organism other than the transgenic animal.

The transgenic mice of the present invention can be immunized with a purified or enriched preparation of CD89 antigen and/or cells expressing CD89 as described previously. The mice will produce B cells which undergo class-switching via intratransgene switch recombination (cis-switching) and express immunoglobulins reactive with CD89. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human $V_L$ or $V_H$ gene segment and a human $J_L$ or $J_L$ segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies which bind to the predetermined antigen can result from isotype switching, such that human antibodies comprising a human sequence γ chain (such as γ1, γ2a, γ2B, or γ3) and a human sequence light chain (such as K) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human sequence antibodies may have binding affinities of at least $1 \times 10^9 M^{-1}$, typically at least $5 \times 10^9 M^{-1}$, frequently more than $1 \times 10^{10} M^{-1}$, and sometimes $5 \times 10^{10} M^{-1}$ to $1 \times 10^{11} M^{-1}$ or greater.

Another aspect of the invention pertains to the B cells from such mice which can be used to generate hybridomas expressing human monoclonal antibodies which bind with high affinity (e.g., greater than $2 \times 10^9$ M$^{-1}$) to CD89. Thus, in another embodiment of the invention, these hybridomas are used to generate a composition comprising an immunoglobulin having an affinity constant ($K_a$) of at least $2 \times 10^9$ M$^{-1}$ for binding CD89, wherein said immunoglobulin comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against CD89 is facilitated by a method for expanding the repertoire of human variable region gene segments in a transgenic mouse having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Some V gene segments may be non-functional (e g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast in no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animal containing rearranged heavy and an unrearranged light immunoglobulin transgene; and IV. Transgenic animals containing rearranged heavy and rearranged light immunoglobulin transgenes.

Of these categories of transgenic animal, the preferred order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Bispecific/Multispecific Molecules Which Bind to CD89

In yet another embodiment of the invention, human monoclonal antibodies to CD89, or antigen-binding portions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding portion of the invention can be functionally linked (e.g., by chemical coupling, genetic fusion, noncovalent association or otherwise) to one or more other binding molecules, such as another antibody, antibody fragment, peptide or binding mimetic. The antibody or antibody fragment also can be linked to an antigen, e.g., a tumor antigen, such that the antigen is targeted to CD89 expressing immune cells, for example, to enhance the process if internalization and presentation of the antigen and, ultimately, to stimulate an immune response.

Accordingly, the present invention includes bispecific and multispecific molecules comprising at least one first binding specificity for CD89 and a second binding specificity for a target cell, e.g., a target epitope of a tumor cell. Bispecific antibodies comprising a murine antibody directed against CD89 and a second antibody directed against a tumor antigen have been demonstrated to be effective anti-tumor agents. See for example, Valerius, T. et al. (1997) *Blood* 90:4485–4492 (describing the anti-tumor activity of an FcαRI×HER-2/Neu bispecific antibody used with or without G-CSF therapy); Elsasser, D. et al. (1999) *Anticancer Res.* 19:1525–1528 (describing the anti-tumor activity of an FcαRI×EGFR bispecific antibody used with or without G-CSF or GM-CSF therapy); Stockmeyer, B. et al. (2000) *J. Immunol.* 165:5954–5961 (describing the anti-tumor activity of an FcαRI×CD20 bispecific antibody used with or without G-CSF or GM-CSF therapy); Stockmeyer, B. et al.

(2001) *J. Immunol. Methods* 248:103–111 (describing the anti-tumor activity of FcαRI×CD20 and FcαRI×HER-2/neu bispecific antibodies used with or without G-CSF or GM-CSF therapy); and Sundarapandiyan, K. et al (2001) *J. Immunol. Methods* 248:113–123 (describing the anti-tumor activity of an FcαRI×CD30 bispecific antibody). The human anti-CD89 antibodies of the invention can be used in the same type of bispecific constructs as anti-tumor agents.

Tumor cells that can be targeted are tumor cells of any type of cancer, including cancer of breast, ovarian, prostate, testicular, lung, colon, rectum, pancreas, liver, central nervous system, kidney, head, neck, bone, blood, and lymphatic system. Preferred target antigens include carcinoembryonic antigen (CEA), gastrin releasing peptide receptor antigen, mucine antigens, EGF-R, HER2/neu, HER3, HER4, CD20, CD30, MAGE antigens, SART antigens, MUC1 antigen, c-erb-2 antigen and TAG 72. TAG 72 is found, e.g., on tumors of the breast, colon, and ovary. An antigen binding region specific for CEA can be, e.g., from the single chain antibody, termed MFE-23, is described in Casey et al. (1994) *J. Immunol. Methods* 179:105 and Chester et al. (1994) *Lancet* 343:455. An anti-HER2/neu antibody is produced by the cell line 520C9 (Ring et al. 1991 J. Immunol. 28: 915–917). Antibody H425 is a humanized version of anti-EGF-R antibody M425. An antibody for TAG 72 is monoclonal antibody cc49 described in published PCT application WO 93/11161, published PCT application WO 90/04410, corresponding to granted EP Patent No. 365 997; published PCT application WO 93/12231; and published PCT application WO 89/01783. Yet other antigens can be antigens associated with B cell lymphomas, e.g., HLA-DR, CD74, CD79, CD20, CD30, CD37, and CD19. Antigens associated with other blood diseases are also within the scope of the invention. Accordingly, the invention also provides methods for treating blood cell disorders, such as leukemias and lymphomas.

Breast and ovarian cancers can be sex hormone dependent cancers. Breast tumors may be characterized by abnormally expressed receptors, e.g. those of the human-EGF-like receptor family (HER), for example HER-2, -3, and 4. The invention is not limited to these embodiments of HER antigens. The natural HER ligand, Heregulin, can be incorporated into a human monoclonal antibody, e.g., bispecific antibody (BsAb) or multispecific molecule, as a means to target a breast tumor cell expressing one or more HER receptor during cancer. Further, heregulin molecules are binding determinants for heterodimeric HER receptors containing, e.g., a monomer of each of HER-2, -3 or -4 in combination. In one embodiment, a monoclonal antibody comprises amino acids 171–239 of the heregulin β2 shown in U.S. Pat. No. 5,367,060. Other portions of heregulin β2, as well as portions of other heregulin molecules, such as those disclosed in U.S. Pat. No. 5,367,060 can also be used.

Antibodies, or antigen-binding portions thereof, of the invention can also be used for treating tumors of the central nervous systems. The nestin protein, which is expressed during normal mammalian fetal development, is expressed on tumors of the central nervous system, including most forms of brain cancer (McKay, D. G. Ronald, U.S. Pat. No. 5,338,839, Aug. 16, 1994). Nestin is also expressed on melanomas on the skin and on melanomas that have metastasized (V. A. Florenes, R. Holm, O. Myklebost, U. Lendahl, O. Fodstad, *Cancer Res.* 54: 354–6, 1994), to other organs and are difficult to detect and treat. The preferred site of delivery for treatment of a brain tumor with the molecules of this invention is directly into the central nervous system or directly, to the brain via spinal injection or fine needle delivery. For a metastatic cancer, a preferred delivery route would be by direct injection into the circulation, or by the ex vivo blood methods described herein.

Other tumor types for which the methods of this invention are exemplified by, but are not limited to, Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840) a pediatric kidney cancer due to occurrence of a somatic mutation in the patient's single copy of a gene normally found in two intact copies. Wilm's tumor can be cured surgically in 95% of cases, and a binding agent is envisioned to be suitable as an adjunct therapeutic modality for surgical patients. Other examples of known cancer-associated proteins for which the compositions of matter and methods of the current invention are suitable include those associated with gastrointestinal cancer (R. Fishel et al., International Application WO 95/14085, 05/26/95), those characterized by development of multiple drug resistance during chemotherapy (J. M. Croop et al., U.S. Pat. No. 5,198,344), and a large number of oncogenes well known to the skilled artisan such as Rb, ras, and c-myc, the sequences of which are available for analysis to those with skill in the art. The compositions of this invention are, for example, suitable for inhibition of secreted enzymes such as matrix metalloproteinases, which are considered to potentiate tumor metastasis (Liotta, L. A., et al., (1991), *Cell*, 64:327–336). In the latter embodiment, a binding agent with a binding determinant to the matrix metalloproteinase and another for FcαR would facilitate inhibition and clearance of these enzymes from in situ activity. If used in conjunction with standard surgical and chemotherapeutic regimens, the compositions are foreseen to reduce cancer re-occurrence and enhance long-term survival.

In addition to tumor cells, the effector cell can be targeted against auto-antibody producing lymphocytes for treatment of autoimmune disease or an IgE-producing lymphocyte for treatment of allergy. Autoimmune disorders which can be treated with a binding agent of the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Thus, an autoimmune disease can be treated by, e.g., administering to a subject having an autoimmune disease an antibody having at least one antigen binding region specific for human CD89 and an antigen binding region specific for an epitope on an autoimmune cell. In one embodiment the target epitope is an epitope on an autoantibody. Accordingly, resting B lymphocytes having autoantibodies on their surface can be targeted and destroyed by a multispecific antibody bridging the B lymphocyte and an effector cell expressing CD89, thereby inducing an effector cell function, resuling in lysis of the B lymphocyte.

Similarly, antibodies having at least one binding specificity for CD89 and at least one binding specificity for an epitope on a lymphocyte producing IgE can be used to treat allergies. The antibody for use in treating allergy in a subject can also be a binding agent having at least one antigen binding region specific for an epitope on an IgE antibody. Accordingly, such a binding agent can link an effector cell expressing CD89 and a target cell whose surface is coated with IgE, such as a basophil and a mast cell, resulting in lysis of the target cells. Such a treatment can also prevent binding of an antigen to the IgE molecules and thus prevent secretion by these cells of mediators involved in allergy, e.g., histamine. Additionally, the antibody can bind soluble IgE and thereby prevent binding of IgE to mast cells and basophils.

The target can also be microorganism (bacterium or virus) or a soluble antigen (such as rheumatoid factor, or other auto-antibodies and toxins). A microorganism is intended to include pathogens, e.g., viruses, bacteria, fungi, protozoa. A microorganism can also be targeted by targeting a cell infected by a microorganism, such as a pathogen infected cell.

Accordingly, the invention provides methods for treating infectious diseases, by, e.g., administering to a subject having an infectious disease an efficient amount of a bispecific molecule of the present invention having at least one antigen binding region specific for CD89 and at least one antigen binding region specific for an epitope on a microorganism. The term "infectious disease" is meant to include disorders caused by one or more species of bacteria, viruses, fungi, and protozoans, which are disease-producing organisms collectively referred to as "pathogens." In this invention, pathogens are exemplified, but not limited to, *Mycobacterium tuberculosis, M. leprae, Pseudomonas aeruginosa, Shigella dysenteria, Salmonella typhi, S. paratyphi, Staphylococcus aureus, Streptococcus hemolyticus, Hemophilus pneumoniae, Escherichia coli* serotype 0157, *Chlamydia* species, *Helicobacter* species; HIV-1,-2, and -3, HTLV, FELV, HSV-I and -II, hepatitis B virus, (e.g., HBV major surface antigen), non-A non-B non-C hepatitis virus, Epstein Barr virus (EBV glycoprotein), pox viruses, rabies viruses; *Aspergillus* species; *Entamoeba histolytica, Giardia* species; Newcastle disease virus; *Toxoplasma gondii*; and *Candida albicans*. Obtaining unique epitopes from these organisms by screening proteins and by assaying peptides in vitro are commonly known to those skilled in the art. Thus, preferred antibodies of the invention have at least one antigen binding region specific for an epitope on any of these microorganisms.

In a preferred embodiment, the antibody has an antigen binding region specific for an envelope glycoprotein of an HIV virus, e.g., gp41 of HIV. Also within the scope of the invention are antibodies specific for gp120 or CD4. In one embodiment, the antibody derives from the human anti-HIV-1 IgG1 mAb, DZ33.

IgA plays an important role in mucosal defense and CD89 has been found on effector cells, e.g., monocytes and macrophages, from mucosal areas (See e.g., Shen, L. and Collins, J. (1989) Immunology 68:491). For example, monocytes and macrophages at mucosal surfaces, e.g., the lung, were found to express CD89 (Shen, L. and Collins, J. (1989) Immunology 68:491). Accordingly, the invention provides methods for eliminating microorganisms or any unwanted cells from mucosal areas. Such methods are particularly useful in view of the fact that mucosal sites are often entry points for invading organisms and further in view of the fact that superoxide is a potent microbial agent. For example, oxygen metabolites, such as superanion have been shown to have bactericidal and bacteriostatic effects.

An antigen binding region to a target epitope can also be a ligand to a receptor, e.g., growth factors or differentiation factors, which can target the binding agent to cells having a receptor for these growth or differentiation factors. For example, an antibody of the present invention can comprise an epidermal growth factor (EGF), or at least a portion or modified form thereof that is capable of interacting with an epidermal growth factor receptor (EGF-R). The antibody can also comprise a binding portion of heregulin. In another preferred embodiment of the invention, the ligand is a small peptide, such as bombesin, gastrin-releasing peptide (GRP), litorin, neuromedin B, or neuromedin C. The sequences of the peptides can be found, e.g., in U.S. Pat. No. 5,217,955, the content of which is incorporated herein by reference. The ligand can also be a modified form of any of these peptides. The modification can increase binding to the receptor, decrease binding, or not affect the binding to a receptor. The modification of the ligand can also transform an agonist into an antagonist, such that the ligand inhibits rather than stimulates cell proliferation. Modification of the ligand can be an addition, a deletion, a substitution, or a modification of at least one amino acid.

Effector cells for targeting can be human leukocytes, preferably macrophages. Other cells include monocytes and other IgA-receptor bearing cells. If desired, effector cells for targeting can be obtained from the host to be treated.

The targeted effector cells, i.e., effector cells coated with binding agent of the invention, can be administered as a suspension of cells in a physiologically acceptable solution. The number of cells administered can be in the order of $10^8-10^9$ but will vary depending on the therapeutic purpose. In general, the amount will be sufficient to obtain localization at the target cell and to effect target cell killing by antibody dependent-mediated cytolysis (ADCC). Routes of administration can also vary. In tumor therapy, for instance, depending upon the localization of a tumor, the targeted effector cells could be administered intravenously, or directly into tumor sites; as for example, directly into the peritoneal cavity in the case of ovarian carcinoma.

Bispecific and multispecific molecules of the invention can further include a third binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target cell antigen. The "anti-enhancement factor portion" can bind an $F_c$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, issued Aug. 7, 1990, the contents of which is expressly incorporated by reference.

While human monoclonal antibodies are preferred, other antibodies which can be employed in the bispecific or multispecific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041–1043); Liu et al. (1987) PNAS 84:3439–3443; Liu et al., 1987, J. Immunol. 139:3521–3526; Sun et al. (1987) PNAS 84:214–218; Nishimura et al., 1987, Canc. Res. 47:999–1005; Wood et al. (1985) Nature 314:446–449; and Shaw et al., 1988, J. Natl Cancer Inst. 80:1553–1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science* 229:1202–1207 and by Oi et al., 1986, *BioTechniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 Nature 321:552–525; Verhoeyan et al. 1988 Science 239:1534; and Beidler et al. 1988 J. Immunol. 141:4053–4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, *Humanized Antibodies to Fc Receptors for Immunoglobulin G on Human Mononuclear Phagocytes.*

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for CD89 and triggers at least one effector function.

Bispecific and multispecific molecules of the present invention can be made using chemical techniques (see e.g., D. M. Kranz et al. (1981) *Proc. Natl. Acad. Sci. USA* 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-target cell and anti-CD89 binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, Mass. et al. (1985) Proc. Natl. Acad. Sci. USA 82:8648). Other methods include those described by Paulus (Behring Ins. Mitt. (1985) No. 78, 118–132); Brennan et al. (Science (1985) 229: 81–83), and Glennie et al. (J. Immunol. (1987) 139: 2367–2375). Preferred conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb× Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multspecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a $\gamma$ counter or a scintillation counter or by autoradiography.

IV. Binding Assays

Several assays can be performed to show that an antibody, or antigen-binding portion thereof, of the present invention specifically bind to CD89, such as human CD89. For example, binding assays comparing binding of the antibody and that of IgA to a variety of cells, some of which are bound by IgA (e.g., monocytes and macrophages) and some of which are not bound by IgA (e.g., K-562 cells), can be performed. The antibody of the invention should bind substantially to the same set of cells as IgA. Competition binding experiments using the antibody and IgA will indicate whether both agents recognize the same epitope. Binding experiments can be flow cytometry experiments, indirect immunofluorescence assays, or ELISAs, among others. Further, IgA and the antibody should immunoprecipitate a protein having similar molecular weight form the same cell. In addition, preclearing with IgA of a cell lysate having CD89 should result in immunoprecipitation of less protein with the antibody than in the absence of preclearing. Similarly, preclearing with the antibody of the cell lysate should result in immunoprecipitation of less protein with IgA than in the absence of preclearing. Other tests for showing that the same antigen is recognized by an antibody, or antigen-binding portion thereof, of the invention and IgA are known in the art. In addition, since CD89 has been cloned, e.g., human CD89, it is possible to use recombinantly produced CD89, or portions thereof, or cells transfected to express CD89 to show binding of an antibody to CD89.

In one embodiment, antibodies of the invention stimulate phagocytosis of target cells by effector cells when the antibody links the target cell to the effector cell. For example, preferred bispecific antibodies of the invention having at least one antigen binding region specific for CD89 and one antigen binding region to an epitope on a target cell can induce phagocytosis of the target cell. In fact, it has been shown that a heteroantibody of My 43 (a mouse anti-CD89 antibody) linked to anti-erythrocyte F(ab)'$_2$ mediates erythrocyte phagocytosis by monocytes. Phagocytosis assays can be performed as follows. Packed target cells, e.g., ox erythrocytes (OE) (10 µl) are mixed for 16 hours at 10° C. with 20 µl of the F(ab')$_2$-Ig conjugates at concentrations previously determined to give maximal rosette formation. Heteroantibody-coated OE are washed, adjusted to 4×10$^7$ cells/ml, and are mixed with an equal volume of myeloid cells at 2×10$^6$ cells/ml. This mixture is incubated for 10 min at 37° C., and the cells are pelleted and incubated for a further 20 min, after which time noningested OE are lysed at 4° C. with buffered ammonium chloride. Phagocytosis can be assessed by microscopic examination of Wright's Giemsa (Sigma) stained cytospin preparations. At least 200 cells are counted in duplicate slides. Phagocytosis can be quantified as the percentage of cells containing one or more ingested erythrocyte(s).

A preferred antibody triggers an oxidative burst, i.e., production of superoxide anion in an effector cell upon binding to CD89 on the effector cell. For example, it was shown that My 43 (a mouse anti-CD89 antibody) triggers production of superoxide anion by interferon-$\gamma$ treated U937 cells.

A superoxide assay can be performed on a solid phase or in solution. A solid phase superoxide assay can be performed as follows. Flat bottom 6-well PVC tissue culture places (Falcon Plastics Baxter Corporation, Bedford, Mass.) can be treated for 30 minutes at room temperature with 1 ml per well of poly-L-lysine (Sigma, St. Louis, Mo.) at 100 µg/ml in PBS. After aspirating dry, glutaradehyde (2%, Sigma) can be added and incubated at room temperature for 15 min. After four washes with PBS, 1 ml of PBS containing the desired amount of Ig can be added, and incubated at ambient temperature for 2 hours. The wells can then be washed with PBS, filled with 100 mM glycine/0.1% BSA in PBS and incubated at 4° C. for 18 hours. They can then be washed twice with PBS and once in Krebs Ringer Hepes buffered salt solution (KRH) and 3×10+6 cells/well were added in KRH containing 1 mM KCN and 1 mg/mnl horse heart ferricytochrome c (Sigma). The cells can be spun down onto the plates for 5 minutes at 100 ×g and incubated at 37° C. PMA (Sigma) as added to positive controls to final concentrations indicated. After 30 min, the contents can be removed, spun down, and the supernatant read at 550 nm in a Dynatech spectrophotometer (Dynatech Labs, Chantilly, Va.).

Suspension superoxide assay can be performed as follows. Cells can be incubated with mAb at 4° C. for 45 minutes, then washed in KRH, resuspended in KRH containing 1 mM KCN and 1 mg/ml horse heart ferricytochrome c (Sigma), and incubation at 37° C. initiated. PMA (Sigma) can be added to positive controls at the concentrations indicated. After 30 minutes, the samples can be removed, spun down, and the supernatant read at 550 nm in a Dynatech spectrophotometer (Dynatech Labs).

V. Antibody Conjugates/Immunotoxins

In another aspect, the present invention features a human anti-CD89 monoclonal antibody, or a fragment thereof, conjugated to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a CD89-related disorder, such as a cancer.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982).

VI. Pharmaceutical Compositions

In another aspect, the present invention provides a composition, e.g., a pharmaceutical composition, containing one or a combination of human monoclonal antibodies, or antigen-binding portion(s) thereof, of the present invention, formulated together with a pharmaceutically acceptable carrier. In a preferred embodiment, the compositions include a combination of multiple (e.g., two or more) isolated human antibodies or antigen-binding portions thereof of the invention. Preferably, each of the antibodies or antigen-binding portions thereof of the composition binds to a distinct, pre-selected epitope of CD89.

In one embodiment, the composition comprises one or a combination of bispecific or multispecific molecules of the invention (e.g., which contains at least one binding specificity for a target cell and at least one binding specificity for CD89).

Pharmaceutical compositions of the invention also can be administered in combination therapy, i.e., combined with other agents. For example, the combination therapy can include a composition of the present invention with at least one anti-tumor agent or other conventional therapy.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesiun, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits tumor growth by at least about 20%, more preferably by at least about 40%, even more preferably by at least about 60%, and still more preferably by at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as manitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VII. Uses and Methods of the Invention

The compositions (e.g., human monoclonal antibodies to CD89 and derivatives/conjugates thereof) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. As used herein, the term "subject" is intended to include human and non-human animals. Preferred human animals include a human patient having disorder characterized by expression, typically aberrant expression (e.g., overexpression) of CD89.

For example, the compositions can be used in vitro or in vivo to diagnose diseases mediated by CD89. The antibodies of the invention can be used to detect levels of CD89, or levels of cells which contain CD89 on their membrane surface, which levels can then be linked to certain disease symptoms. Alternatively, the antibodies can be used to inhibit or block CD89 function which, in turn, can be linked to the prevention or amelioration of certain disease symptoms, thereby implicating CD89 as a mediator of the disease. This can be achieved by contacting a sample and a control sample with the anti-CD89 antibody under conditions that allow for the formation of a complex between the antibody and CD89. Any complexes formed between the antibody and CD89 are detected and compared in the sample and the control.

In another embodiment, human antibodies, or binding portions thereof, of the present invention can be used to modulate CD89 levels on effector cells, such as by capping and eliminating receptors on the cell surface. Mixtures of anti-Fc receptor antibodies can also be used for this purpose.

Further within the scope of the invention are methods for treating a disorder, such as an autoimmune disorder, a cancer, or a pathogenic infection with the bispecific and multispecific human antibodies described above. Such antibodies include at least one binding specificity for CD89 and at least one binding specificity for an antigen binding region to a target antigen. In another embodiment, the antibody includes a third binding specificity to a binding specificity for an antigen binding region to a different epitope of the same target antigen and/or receptor. Methods for eliminating unwanted cells, i.e., target cells, or antigen in a subject includes treating the subject with the bispecific or multispecific antibodies of the invention. In one embodiment, methods include obtaining an aliquot of a sample of blood or blood cells from a subject, treating the blood or blood cells ex vivo with a therapeutically effective dose of a bispecific or multispecific antibody of the invention in a pharmaceutically acceptable carrier, and returning the treated blood or blood cells to the subject. Preferably, the cells of the sample of blood are isolated and expanded in culture and, more preferably, the cells of the sample of blood are treated with agents that enhance the number or activity of CD89. Such agents include cytokines, lymphokines, or growth factors, e.g., G-CSF, GM-CSF, IFN-γ, TNF, and interleukins such as IL-2, IL-10, and IL-12.

In another embodiment, the invention provides methods for immunizing a subject against a cancer antigen, an antigen found on a pathogen or a cell infected by a pathogen. Such methods include administering in a pharmaceutically acceptable carrier a composition comprising a bispecific or multispecific antibody having a binding specificity for CD89 and a binding specificity for an epitope of a pathogenic infectious organism, or of an antigen of an infected cell, or of a cancer cell to a subject. Alternatively, the composition can comprise an anti-CD89 antibody linked to one or more antigens of a pathogenic infectious organism, or of an antigen of infected cells, or of a cancer cell.

In another embodiment, human antibodies of the present invention which block or inhibit IgA binding to CD89 are used in the treatment of diseases characterized by abnormal endogenous IgA, such as diseases characterized by circulating IgA-containing complexes and/or precipitation of IgA-immune complexes, e.g., chronic hepatitis, Henoch-Schonlein purpura (HSP), IgA nephropathy (Berger's disease), or IgA-glomerulonephritis. Human anti-CD89 antibodies of the invention can be administered to patients suffering from such disorders to inhibit or downregulate the binding of endogenous IgA to CD89. For example, although not intending to be limited by mechanism, administration of an anti-CD89 antibody of the invention can result in blocking of CD89 such that the endogenous abnormal IgA is unable to engage the receptors and thus unable to trigger undesirable effector functions.

In another embodiment, the human monoclonal antibodies of the present invention have the advantage of not inducing, or inducing only to a minimal extent, complement-mediated lysis of cells and, therefore, have fewer side effects in triggering complement-activated afflictions, such as, for example, acne.

Suitable methods of administering the compositions (e.g., human antibodies, multispecific and bispecific molecules) of the invention are known in the art of antibody-based therapies. Suitable dosages of the molecules used will depend on the age and weight of the subject and the particular drug used. The molecules can be coupled to radionuclides, such as 131I, 90Y, 105Rh, etc., as described in Goldenberg, D. M. et al. (1981) Cancer Res. 41: 4354–4360, and in EP 0365 997. The compositions (e.g, human antibodies, multispecific and bispecific molecules) of the invention can also be coupled to anti-infectious agents.

Human anti-CD89 antibodies, or antigen binding fragments thereof, also can be co-administered with another therapeutic agent, e.g., a cytokine or a chemotherapeutic agent, or can be co-administered with other known therapies, e.g., an anti-cancer therapy, e.g., radiation. Such therapeutic agents include, among others, cytokines such as G-CSF, GM-CSF, IL-2, IFN-γ and IFN-α, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60–75 mg/m$^2$ dose once every 21 days. Co-administration of the human anti-CD89 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

The compositions (e.g, human antibodies, multispecific and bispecific molecules) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Also within the scope of the invention are kits comprising the compositions (e.g., human antibodies, multispecific and bispecific molecules) of the invention and instructions for use. The kit can further contain a least one additional reagent, such as complement, or one or more additional human antibodies of the invention (e.g, a human antibody having a complementary activity which binds to an epitope of a CD89 antigen which is distinct from the first human antibody).

The compositions (e.g., human antibodies, multispecific, and bispecific molecules) of the invention can also be used to target cells expressing CD89, for example, for labeling such cells. For such use, the binding agent can be linked to a molecule that can be detected. Thus, the invention provides methods for localizing ex vivo or in vitro cells expressing CD89. The detectable label can be, e.g., a radioisotope, a fluorescent compound, an enzyme, or an enzyme co-factor.

In one embodiment, the invention provides methods for detecting the presence of CD89 antigen in a sample, or measuring the amount of CD89 antigen, comprising contacting the sample, and a control sample, with a human monoclonal antibody, or an antigen binding portion thereof, which specifically binds to CD89, under conditions that allow for formation of a complex between the antibody or portion thereof and CD89. The formation of a complex is then detected, wherein a difference complex formation between the sample compared to the control sample is indicative the presence of CD89 antigen in the sample.

In still another embodiment, the invention provides a method for detecting the presence or quantifying the amount of Fc-expressing cells in vivo or in vitro. The method comprises (i) administering to a subject a composition (e.g., a multi- or bispecific molecule) of the invention or a fragment thereof, conjugated to a detectable marker; (ii) exposing the subject to a means for detecting said detectable marker to identify areas containing Fc-expressing cells.

The present invention is further illustrated by the following examples which should not be construed as further limiting. The contents of all figures and all references, patents and published patent applications cited throughout this application are expressly incorporated herein by reference.

EXAMPLES

Example 1

Generation of Transgenic (Cmu Targeted) Mice for the Production of Fully Human Monoclonal Antibodies to CD89

Construction of a CMD Targeting Vector

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEM19H (Marsh et al; Gene 32, 481–485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in E. coli.

The targeting vector was constructed as follows. A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the SmaI site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65–74) and containing the pgk polyadenylation site (PvuII/HindIII fragment; Boer et al. (1990) Biochemical Genetics 28: 299–308). This cassette was obtained from the plasmid pKJ1 (described by Tybulewicz et al. (1991) Cell 65: 1153–1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al. (1988) Nature 336: 348–352. This cassette consists of the coding sequences of the tk gene bracketed by the mouse pgk promoter and polyadenylation site, as described by Tybulewicz et al. (1991) Cell 65: 1153–1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells

AB-1 ES cells (McMahon, A. P. and Bradley, A., (1990) Cell 62: 1073-1085) were grown on mitotically inactive SNL76/7 cell feeder layers (ibid.) essentially as described (Robertson, E. J. (1987) in *Teratocarcinomas and Embryonic Stem Cells: a Practical Approach* (E. J. Robertson, ed.) Oxford: IRL Press, p. 71–112). The linearized CMD targeting vector was electroporated into AB-1 cells by the methods described Hasty et al. (Hasty, P. R. et al. (1991) Nature 350: 243–246). Electroporated cells were plated into 100 mm dishes at a density of $1-2\times10^6$ cells/dish. After 24 hours, G418 (200 micrograms/ml of active component) and FIAU ($5\times10^{-7}$ M) were added to the medium, and drug-resistant clones were allowed to develop over 8–9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) Nucleic Acids Res. 19: 4293). Isolated genomic DNA was digested with SpeI and probed with a 915 bp SacI fragment, probe A (see FIG. 1), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb SpeI band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmu1 exon.

Generation of Mice Bearing the Mutated mu Gene

The three targeted ES clones, designated number 264, 272, and 408, were thawed and injected into C57BL/6J blastocysts as described by Bradley (Bradley, A. (1987) in *Teratocarcinomas and Embryonic Stem Cells: a Practical Approach.* (E. J. Robertson, ed.) Oxford: IRL Press, p. 113–151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of mu Gene

To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647–656). Four agouti offspring were generated. Serum was obtained from these animals at the age of 1 month and assayed by ELISA for the presence of murine IgM. Two of the four offspring were completely lacking IgM (see Table 1). Genotyping of the four animals by Southern blot analysis of DNA from tail biopsies by BglI digestion and hybridization with probe A (see FIG. 1), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

TABLE 1

| Mouse | Serum IgM (micrograms/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Table 1 shows the levels of serum IgM, detected by ELISA, for mice carrying both the CMD and JHD mutations (CMD/JHD), for mice heterozygous for the JHD mutation (+/JHD), for wild type (129Sv×C57BL/6J)F1 mice (+/+), and for B cell deficient mice homozygous for the JHD mutation (JHD/JHD).

Example 2

Generation of HCO12 Transgenic Mice for the Production of Fully Human Monoclonal Antibodies to CD89

The HCO12 Human Heavy Chain Transgene

The HCO12 transgene was generated by coinjection of the 80 kb insert of pHC2 (Taylor et al., 1994, Int. Immunol., 6: 579–591) and the 25 kb insert of pVx6. The plasmid pVx6 was constructed as described below.

An 8.5 kb HindIII/SalI DNA fragment, comprising the germline human VH1-18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human VH5-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287–6295), to generate the plasmid p251f. A new cloning vector derived from pGP1f pGP1k, was digested with EcoRV/BamHI, and ligated to a 10 kb EcoRV/BamHI DNA fragment, comprising the germline human VH3-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16.

A clone was obtained with the VH1-18 gene in the same orientation as the other two V genes. This clone, designated pVx6, was then digested with NotI and the purified 26 kb insert coinjected—together with the purified 80 kb NotI insert of pHC2 at a 1:1 molar ratio—into the pronuclei of one-half day (C57BL/6J×DBA/2J)F2 embryos as described by Hogan et al. (B. Hogan et al., Manipulating the Mouse Embryo, A Laboratory Manual, $2^{nd}$ edition, 1994, Cold Spring Harbor Laboratory Press, Plainview, N.Y.). Three independent lines of transgenic mice comprising sequences from both Vx6 and HC2 were established from mice that developed from the injected embryos. These lines are designated (HCO12) 14881, (HCO12) 15083, and (HCO12) 15087. Each of the three lines were then bred with mice comprising the CMD mutation described in Example 1, the JKD mutation (Chen et al. 1993, EMBO J. 12: 811–820), and the (KCo5)9272 transgene (Fishwild et al. 1996, Nature Biotechnology 14: 845–851). The resulting mice express human immunoglobulin heavy and kappa light chain transgenes in a background homozygous for disruption of the endogenous mouse heavy and kappa light chain loci.

Example 3

Production of Human Monoclonal Antibodies and Bispecifics Against CD89

Human anti-CD89 monoclonal antibodies were generated by immunizing HCO12 mice with recombinant soluble CD89 antigen.

In particular, HCO12 mice were initially immunized with 20 µg antigen emulsified in Complete Freund's Adjuvant, followed by two more immunizations in Incomplete Freund's Adjuvant. Mice were immunized every 2 weeks by intrapertineal injections.

Ten days after the final immunization, the human IgG anti-CD89 titer was determined by ELISA (as described below). Mice that developed sufficient titer (anti-CD89 IgG response) were IV boosted with 23 µg antigen at three days and two days prior to splenectomy. The spleens from responding mice were harvested and dispersed into single cells.

To generate hybridomas producing anti-CD89 antibodies, splenocytes from mice with plasma containing anti-CD89 antibodies were fused with P3X63-Ag8.653 cells (deposited with the ATCC under designation ATCC CRL 1580 nonsecreting mouse myeloma cells) and PEG. After hybridomas grew out, each well containing hybridomas was screened for the production of human IgG using an anti-human IgG ELISA. Positive hybridomas were screened for and selected based on the following properties: (1) production of human IgG1κ antibodies, (2) binding to soluble recombinant CD89, and (3) binding to CD89-expressing immune cells. Three positive clones, referred to as 7.4 (7F 12), 8.2 (8D2) and 14.1 (14A8) were found to fit these criteria.

Solid-phase ELISA based assays were employed in the binding studies. Briefly, soluble recombinant CD89 in PBS was coated onto 96-well microtiter plates (1 µg/ml) and incubated overnight at room temperature. The plates were then washed with PBS-0.2% Tween-20 (PBST) and blocked with chicken serum albumin in PBST for 1 hour at room temperature. Supernatants from the anti-CD89 producing hybridomas or purified antibody (in PBS) were added to the wells and incubated for 2 hours at room temperature. The plates were washed with PBST as above and then incubated with 50 µl of HRP-conjugated goat-anti-human for 1 hour at room temperature. After washing, 100 µl of ABTS (150 mg 2,2'-azino-bis (3-ethylbenzthiazoline-6-sulfonic acid in 500 ml of 0.1 M citric acid, pH 4.35)/$H_2O_2$ (10 µl 30% $H_2O_2$ per 10 ml of ABTS solution) chromagen/substrate solution was added to each well and the samples read with a microplate reader at a wavelength of 405 nm.

Hybridomas which produced human IgG that bound CD89 were further characterized for isotype using ELISA (Human Kappa) (same protocol described above). Three cell lines, 7.4, 8.2 and 14.1, were selected based on the production of antibodies that bind soluble CD89 having human IgG1κ isotype. Antibodies were isolated from a Cellmax bioreactor (Cellco, Laguna Hills, Calif.) using HyQ-CCM1 medium containing 1 to 5% Fetalclone (Hyclone, Logan, Utah) and purified by column chromatography. Purified antibodies were extensively dialyzed against 0.3 M sodium carbonate buffer, pH 9.5, for labeling with fluorescence isothiocyanate (FITC). A stock FITC solution was prepared by dissolving 1 mg solid FITC in 1 ml of DMSO. Stock FITC was added dropwise with constant mixing in an amount to provide 50 µg FITC per mg of antibody protein. Following the addition of FITC, the solution was incubated in the dark for 1–3 hours at room temperature. FITC labeled antibodies were isolated by gel filtration on a Sephadex G-10 column equilibrated in PBS.

Purified antibodies were further characterized for binding specificity and activity as described in the following examples.

Example 4

Characterization of Human Monoclonal Antibodies to CD89

1. Binding/Specificity Studies

Monoclonal antibodies (Mabs) purified from hybridoma supernatants that showed significant binding to CD89 as detected by ELISA (e.g., 7.4, 8.2 and 14.1) were further tested as described below using flow cytometry (FACS analysis) and confirmed to bind to the following CD89 expressing cells: (1) murine 2a1.6 cells transformed to express human CD89 ("2a1.6/CD89 cells"), (2) human PMNL cells ("HuPMN") and (3) PMNL cells isolated from transgenic mice expressing human CD89 ("FcαRITg MsPMN").

MAb 14.1, in particular, was confirmed to recognize CD89 (FcαRI) within extracellular domain 2, outside the IgA-binding site which distinguishes it from known murine anti-CD89 Mabs, such as My43 (mouse IgM) which blocks the FcαRI ligand-binding domain (Shen, L. et al., 1989 *J. Immunol.* 143: 4117).

PMNL Isolation

Human PMNL were isolated from heparinized venous blood of healthy volunteers by Ficoll-Histopaque (Sigma) density gradient centrifugation. PMNL purify determined by cytospin preparations exceeded 95%, and cell viability was >98% (determined by trypan blue exclusion).

Prior to niurine PMNL isolation, mice were injected subcutaneously with 15 µg polyethylene-glycol granulocyte colony-stimulating growth factor (PEG-G-CSF, kindly provided by Dr. J. Andreson, Amgen, Thousand Oaks, Calif.) to increase PMNL numbers. Blood was collected from the retro-orbital plexus 3 days later. Erythrocytes were removed by hypotonic lysis, followed by washing remaining leukocytes three (3) times with RPMI 1640 medium (Gibco BRL, Grand Island, N.Y.), supplemented with 10% FCS. FACS analyses, performed on a FACSsan (Becton Dickinson, San Jose, Calif.), revealed leukocytes to consist of ~55% PMNL, ~40% lymphocytes, ~3% monocytes, and ~1% cosinophils. Cell viability determined by trypan blue exclusion was always >95%.

FACS Analysis 1 (Binding Study)

50 microliters antibody dilution was added to 50,000 2a1.6/CD89 cells in 50 microliters Facsbuffer and incubated for thirty (30) minutes at 4° C. The cells were then washed three (3) times with 100 microliters Facsbuffer, incubated with Rabbit (Fab2) anti Hu IgG-FITC for thirty (30) minutes at 4° C., and washed three (3) times with 100 microliters Facsbuffer. The cells were resuspended in 200 microliters Facsbuffer. Fluorescence was determined on a Facscalibur (Becton Dickinson).

FACS Analysis 2 (Specificity Study 1)

25 microliters of 1 mg/ml in Facsbuffer were added to 50,000 2a1.6/CD89 cells in 50 microliters Facsbuffer and incubated for fifteen (15) minutes at 4° C. 25 microliters antibody dilution were added and incubated for thirty (30) minutes at 4° C. and washed three (3) times with 100 microliters Facsbuffer. The cells were then incubated with Rabbit(Fab2) anti Hu IgG-FITC for thirty (30) minutes at 4° C., washed three (3) times with 100 microliters Facsbuffer, and resuspended in 200 microliters Facsbuffer. Fluorescence was determined on a Facscalibur (Becton Dickinson).

FACS Analysis 3 (Specificity Study 2)

50 microliters antibody dilution were added to 50,000 2a1.6/CD89 cells, as well as contol cells: Jurkat/IIIa, CHO/IIIbNA.2, CHO/IIIbNA. 1, 2a1.6/CD64 or SLC cells in 50 microliters Facsbuffer, incubated for thirty (30) minutes at 4° C., and washed three (3) times with 100 microliters Facsbuffer. Cells were then incubated with Rabbit (Fab2) anti Hu IgG-FITC for thirty (30) minutes at 4° C., and washed three (3) times with 100 microliters Facsbuffer. Cells were resuspended in 200 microliters Facsbuffer. Fluorescence was determined on a Facscalibur (Becton Dickinson).

FACS Analysis 4 (Whole Blood Binding Study)

50 microliters antibody dilution were added to 50 microliters Human, Mouse or CD89 Tg mouse whole blood and incubated for thirty (30) minutes at 4° C. Cells were lysed with FACS lysis buffer, incubated at 4° C., washed three (3) times with 100 microliters Facsbuffer, incubated with Rabbit (Fab2) anti Hu IgG-FITC for thirty (30) minutes at 4° C., and washed three (3) times with 100 microliters Facsbuffer. Cells were then resuspended in 200 microliters Facsbuffer. Fluorescence was determined on a Facscalibur (Becton Dickinson).

II. Competition Studies

Mabs 14.1 and 7.4 were tested in blocking studies and inhibition ELISA as described below for the ability to inhibit human IgA and Mab My43 (a mouse anti-CD89 antibody) binding to CD89.

Like IgA, MY43 binds to CD89 at the natural ligand binding site and thus competes with IgA binding. Mabs 14.1 and 7.4 were also tested for the ability to inhibit binding of Mabs A77 and A59 (which binds outside the natural ligand, IgA, binding site) to CD89.

Mab 14.1 did not inhibit IgA and MY43 binding, but did inhibit A77 and A59 binding to CD89, showing that it binds outside the natural ligand binding site.

Mab 7.4 did not inhibit IgA, MY43, A77 or A59 binding to CD89, showing that it also binds outside the natural ligand binding site, but at a site different from 14.1.

Blocking Study 25 microliters antibody dilution were added to 50,000 2a1.6/cd89 cells in 50 microliters Facsbuffer and incubated for fifteen (15) minutes at 4° C. 25 microliters of a suboptimal concentration of A77-FITC, A59-PE or MY43 were added and incubated for thirty (30) minutes at 4° C. and washed three (3) times with 100 microliters Facsbuffer. The MY43 treated cells were incubated with Rabbit (Fab2) anti Hu-IgG-Fc-FITC for thirty (30) minutes at 4° and washed three (3) times with 100 microliters Facsbuffer. The cells were then resuspended in 200 microliters Facsbuffer. Fluorescence was determined on a Facscalibur (Becton Dickinson).

Inhibition ELISA

A 96 well ELISA (flat) bottom plate was coated with 100 microliters/well soluble recombinant CD89 (1 microgram/ml) in PBS and incubated overnight at room temperature. The ELISA plate was emptied and incubated with 100 microliters/well PBS/0.05% Tween 1% Chicken serum (PBST/Ch) for sixty (60) minutes at room temperature. The plate was emptied and incubated with an excess of antibody (50 microliters/well) which was diluted in PBST/Ch for ten (10) minutes. 50 microliters per well of an aIgA2 solution were added in PBST/Ch in a doses response and incubated for sixty (60) minutes at room temperature. The plate was then washed three (3) times with PBS/0.05% Tween (PBST) and incubated with 4E8-biotin 100 microliters per well (Mouse anti IgA) for sixty (60) minutes at room temperature. The plate was then washed three (3) times with PBST and incubated with Strep-HRP in PBST/Ch 100 microliters per well for sixty (60) minutes at room temperature, washed three (3) times with PBST and developed ELISA with ABTS. Optical density was read at a wavelength of 405 nm in a Bio-tek reader.

III. Immuno Precipitation Studies

Mabs 14.1 and 7.4 were found to immunoprecipitate soluble recombinant CD89 (sCD89).

Briefly, a ProtG Sepharose Fast Flow column was washed three (3) times with PBS. sCD89 was precleared with washed beads in PBS for two (2) hours at 4° C. The precleared sCD89 was incubated for two (2) hours at 4° C. with antibodies, mouse IgG or human IgG. The CD89/IgG solution was washed with Prot G for one (1) hour at 4° C. and then washed five (5) times with PBS. The samples were then resuspended in SDS-PAGE sample buffer, run in a SDS-PAGE gradient gel and then the gel was stained with Commassie Brilliant Blue.

IV. Affinity Studies

The affinity kinetics, i.e., binding equilibrium association constant (Ka) and dissociation constant (Kd), of MAbs 14.1 and 7.4 were measured as described below.

The Ka for Mab 14.1 was determined to be about $1.5 \times 10^9$ and the Kd about $6.8 \times 10^{-10}$.

The Ka for MAb 7.4 was determined to be about $2.0 \times 10^8$ and the Kd about $5.1 \times 10^{-9}$.

Affinity kinetics were determined using a BIAcore assay by immobilizing sCD89 to chips and flowing the Mabs over the chips at various concentrations. Mab capture assays were also performed by flowing sCD89 over MAbs. Immobilization of the antigen and human IgG was performed through amine coupling. The kit was purchased through BIAcore, including chips and buffer. A langmuir model was used as the fit. Analysis of the data was performed through the models available on the software associated with the instrument.

Example 5

Activity of Human Monoclonal Antibodies to CD89

I. Calcium flux Studies

Mab 14.1 was tested as follows and shown to induce a calium flux. Mab 7.4 did not induce a calcium flux.

38 microliters SNARF-1 and 38 microliters FLUO-3 were added to resuspended 3e6 cells in 1.52 ml medium without serum, after washing the cells three (3) times. The cells were incubated in the dark at 37° C. and 5 ml warm (37°) medium without serum were added and the cells were incubated for another five (5) minutes at 37° C. The cells were then washed twice with medium without serum and coated with antibody anti FcαR1 and washed again. The cells in Ca++ Mobilisation buffer were resuspended and run on a flow cytometer for twenty-four (24) seconds to establish the baseline level. Next, crosslinking antibody anti HuIgG-Fc cells were added and monitored for four (4) minutes. Cells used were not incubated with anti FcαR1 in order to establish negative control.

II. Human C1q Binding Studies

Mabs 14.1 and 7.4 were tested by ELISA and FACS as described in the subsections below for the ability to fix hC1q in ELISA and when bound to CD89 expressing cells (in FACS analysis).

Mab 14.1 was able to fix hC1q in ELISA and weakly when bound to cells. Mab 7.4 was able to fix hC1q in ELISA, but not when bound to cells. The inability of these Mabs to fix hC1q when bound to cells, which mirrors in vivo conditions, makes them particularly valuable for use in therapy, e.g., in situations where it is undesirable to initiate the complement cascade (resulting in target cell lysis).

ELISA Analysis

Briefly, a 96 well ELISA (flat) bottom plate was coated with 100 microliter/well human IgG (3 microgram/ml) in PBS (hIgG1, hIgG2, hIgG3 and hIGg4 were used as controls), incubated overnight at room temperature and emptied and then incubated with 100 microliter/well Phosphate/NaCl/Gelatin/Tween buffer (C1q-ELISA diluent) for sixty (60) minutes at room temperature. The plate was emptied and incubated with 20 microgram/ml (100 microliter/well), diluted in C1a-ELISA diluent for sixty (60) minutes at room temperature, and washed three (3) times with C1q-ELISA diluent. Next, the plate with Rabbit anti hC1q diluted in C1q-ELISA diluent 100 microliter per well was incubated for sixty (60) minutes at room temperature, washed three (3) times with C1q-ELISA diluent and incubated with PO-conjugated Swine anti Rb IgG-Fc diluted in C1q-ELISA diluent 100 microliter per well for sixty (60) minutes at room temperature. The plate was then washed three (3) times with C1q-ELISA diluent. The ELISA was developed with ABTS and the optical density was read at a wavelength of 405 nm in Bio-tek reader.

FACS Analysis 25 microliters antibody dilution in C1q-Facsbuffer were added to 50,000 2a1.6/cd89 cells in 50 microliter Facsbuffer plus NaCl (C1q-Facsbuffer), incubated for fifteen (15) minutes at 4° C. to which 25 microliter of hC1q (20 microgram/ml) in C1q-Facsbuffer were added and incubated for thirty (30) minutes at 4° C. The cells were then washed three (3) times with 100 microliter C1q-Facsbuffer, incubated with Rabbit anti hC1q-Fitc for thirty (30) minutes at 4° C. and washed three (3) times with 100 microliter C1q-Facsbuffer. The cells were resuspended in 200 microliter C1q-Facsbuffer. Fluorescence was determined on a Facscalibur (Becton Dickinson).

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An isolated human monoclonal antibody, or antigen binding portion thereof, selected from the group consisting of:
   (a) an antibody, or antigen binding portion thereof, comprising (i) a heavy chain variable region comprising CDR1, CDR2, and CDR3 sequences comprising amino acid residues 30–35, amino acid residues 50–66, and amino acid residues 99–108 of SEQ ID NO:2, respectively; and (ii) a light chain variable region comprising CDR1, CDR2, and CDR3 sequences comprising amino acid residues 24–34, amino acid residues 50–56, and amino acid residues of 89–97 of SEQ ID NO:4, respectively, wherein the antibody binds to human CD89; and
   (b) an antibody, or antigen binding portion thereof, comprising (i) a heavy chain variable region comprising CDR1, CDR2, and CDR3 sequences comprising amino acid residues 31–35, amino acid residues 50–66, and amino acid residues 99–108 of SEQ ID NO:6, respectively; and (ii) a light chain variable region comprising CDR1, CDR2, and CDR3 sequences comprising amino acid residues 24–35, amino acid residues 51–57, and amino acid residues 90–99 of SEQ ID NO:8, respectively, wherein the antibody binds to human CD89.

2. An isolated human monoclonal antibody, or antigen binding portion thereof, comprising a human heavy chain variable region and a human light chain variable region, wherein:
   (a) the human heavy chain variable region comprises the amino acid sequence of SEQ ID NO:2;
   (b) the human light chain variable region comprises the amino acid sequence of SEQ ID NO:4;
   (c) the antibody binds to human CD89;
   (d) the antibody does not activate complement upon binding to CD89 in vivo; and
   (e) the antibody does not block IgA binding to CD89.

3. An isolated human monoclonal antibody, or antigen binding portion thereof, comprising a human heavy chain variable region and a human light chain variable region, wherein:
   (a) the human heavy chain variable region comprises the amino acid sequence of SEQ ID NO:6;
   (b) the human light chain variable region comprises the amino acid sequence of SEQ ID NO:8;
   (c) the antibody binds to human CD89;
   (d) the antibody does not activate complement upon binding to CD89 in vivo; and
   (e) the antibody does not block IgA binding to CD89.

4. An isolated human monoclonal antibody, or antigen binding portion thereof, comprising human heavy chain and human light chain variable regions comprising the amino acid sequences shown in SEQ ID NO:2 and SEQ ID NO:4, respectively.

5. An isolated human monoclonal antibody, or antigen binding portion thereof, comprising human heavy chain and human light chain variable regions comprising the amino acid sequences shown in SEQ ID NO:6 and SEQ ID NO:8, respectively.

6. A composition comprising a pharmaceutically acceptable carrier and an isolated human monoclonal antibody, or antigen binding portion thereof, comprising:
   (a) a heavy chain variable region derived from a human germline $V_H$ 3-30.3 gene; and
   (b) a light chain variable region derived from a human germline $V_K$ L18 gene or $V_K$ A27 gene;
   wherein the human antibody binds human CD89.

7. An isolated human monoclonal antibody, or antigen binding portion thereof, comprising:
   (a) a heavy chain variable region derived from a human germline $V_H$3-30.3 gene; and
   (b) a light chain variable region is derived from a human germline $V_K$ L18 gene;
   wherein the human antibody binds human CD89 and wherein the antibody does not activate complement upon binding to CD89 in vivo.

8. The antibody, or antigen binding portion thereof, of claim 1, 2, or 3, wherein the antigen binding portion thereof, is a Fab fragment or a single chain antibody.

9. A hybridoma comprising a B cell obtained from a transgenic nonhuman animal having a genome comprising a human heavy chain transgene and a light chain transgene fused to an immortalized cell, wherein the hybridoma produces a detectable amount of the antibody, or antigen binding portion thereof, of claim 1, 2, or 3.

10. A transfectoma comprising nucleic acids encoding a human heavy chain and a human light chain, wherein the transfectoma produces a detectable amount of the antibody, or antigen binding portion thereof, of claim 1, 2, or 3.

11. A method of producing the antibody, or antigen binding portion thereof, of claim 1, 2, or 3, comprising:
   immunizing a transgenic nonhuman animal having a genome comprising a human heavy chain transgene and a human light chain transgene with human CD89 or a cell expressing human CD89, such that antibodies are produced by B cells of the animal;
   isolating B cells of the animal;
   fusing the B cells with myeloma cells to form immortal, hybridoma cells that secrete human monoclonal antibodies specific for CD89; and
   isolating the human monoclonal antibodies specific for CD89 from the culture supernatant of the hybridoma.

12. A composition comprising the antibody, or antigen binding portion thereof, of claim 1, 2, 3 and a pharmaceutically acceptable carrier.

13. A composition comprising a combination of two or more antibodies, or antigen binding portions thereof, of claim 1, 2, or 3, wherein each of said antibodies, or antigen binding portions thereof, binds to a distinct epitope of human CD89.

14. The composition of claim 12 further comprising a cytotoxic agent.

15. A method of detecting the presence of CD89 or a cell expressing CD89 in a sample, comprising:

contacting the sample with the antibody, or antigen binding portion thereof, of claim 1, 2, or 3 under conditions that allow for formation of a complex between the antibody, or antigen binding portion thereof, and CD89; and detecting the formation of the complex.

16. An isolated human monoclonal antibody, or antigen binding portion thereof, comprising:
(a) a heavy chain variable region derived from a human germline $V_H$ 3-303 *gene*;
(b) a light chain variable region derived from a human germline $V_K$ A27 gene;
wherein the human antibody binds human CD89.

* * * * *

UNITED STATES PATENT AND TRADEMARK OFFICE
CERTIFICATE OF CORRECTION

PATENT NO. : 7,192,582 B2  Page 1 of 1
APPLICATION NO. : 10/073644
DATED : March 20, 2007
INVENTOR(S) : Debra Hudson et al.

It is certified that error appears in the above-identified patent and that said Letters Patent is hereby corrected as shown below:

In Claim 16, column 60, line 7, replace "$V_H$ 3-303" with --$V_H$ 3-30.3--

Signed and Sealed this

Seventh Day of August, 2007

JON W. DUDAS
*Director of the United States Patent and Trademark Office*

SEQUENCE LISTING

```
<160> NUMBER OF SEQ ID NOS: 8
<210> SEQ ID NO 1
<211> LENGTH: 357
<212> TYPE: DNA
<213> ORGANISM: Homo sapiens

<400> SEQUENCE: 1
caggtgcaac tggtggagtc tgggggaggc gtggtccagc ctgggaggtc cctgagactc      60
tcctgtgcag cctctggatt caccttcagt agttatgttc tgcactgggt ccgccaggct     120
ccaggcaagg ggctggattg ggtggcagtg atatcagatg atggaaggaa taaatacttc     180
gcagactccg tgaagggccg attcaccatc tccagagaca attccaagaa cacgctgtat     240
ctgcaaatga acagcctgag agctgaggac acggctgtgt attactgtgt gagagaaggg     300
tatagcggca gctggtttga ctactggggc cagggaaccc tggtcaccgt ctcctca       357

<210> SEQ ID NO 2
<211> LENGTH: 119
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
                20                  25                  30
Val Leu His Trp Val Arg Gln Ala Pro Gly Lys Gly Leu Asp Trp Val
         35                  40                  45

Ala Val Ile Ser Asp Asp Gly Arg Asn Lys Tyr Phe Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Glu Gly Tyr Ser Gly Ser Trp Phe Asp Tyr Trp Gly Gln Gly
            100                 105                 110

Thr Leu Val Thr Val Ser Ser
        115

<210> SEQ ID NO 3
<211> LENGTH: 321
<212> TYPE: DNA
<213> ORGANISM: Homo sapiens

<400> SEQUENCE: 3
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatggt gcctccagtt tggaaggtgg ggtcccatca     180
aggttcagcg gcagtggatc tgggacagat tcactctca ccatcagcag cctgcagcct     240
gaagattttg caacttatta ctgtcaacag tttaatagtt acccattcac tttcggccct     300
gggaccaaag tggatatcaa a                                                321

<210> SEQ ID NO 4
<211> LENGTH: 107
<212> TYPE: PRT
<213> ORGANISM: Homo sapiens

<400> SEQUENCE: 4

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Gly Ala Ser Ser Leu Glu Gly Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Phe
                 85                  90                  95

Thr Phe Gly Pro Gly Thr Lys Val Asp Ile Lys
            100                 105

<210> SEQ ID NO 5
<211> LENGTH: 357
<212> TYPE: DNA
<213> ORGANISM: Homo sapiens

<400> SEQUENCE: 5
caggtgcagc tggtggagtc tgggggaggc gtggtccagc ctggagggtc cctgagactc      60
```

-continued

```
tcctgtgcag cctctggatt caccttcagt agctatgcta tgcactgggt ccgccaggct      120
ccaggcaagg ggctggagtg ggtggcagtt atatcatatg atggaagaaa taaagactac      180
gcagactccg tgaagggccg attcaccatc tccagagaca attccaagaa cacgctgtat      240
ctgcaaatga acagcctgag agctgaggac acggctgtgc attactgtgc gaggcttgac      300
tggggatatg atgcttttga tatctggggc caagggacaa tggtcaccgt ctcttca       357
```

<210> SEQ ID NO 6
<211> LENGTH: 119
<212> TYPE: PRT
<213> ORGANISM: Homo sapiens

<400> SEQUENCE: 6

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Arg Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val His Tyr Cys
                85                  90                  95

Ala Arg Leu Asp Trp Gly Tyr Asp Ala Phe Asp Ile Trp Gly Gln Gly
            100                 105                 110

Thr Met Val Thr Val Ser Ser
        115

<210> SEQ ID NO 7
<211> LENGTH: 327
<212> TYPE: DNA
<213> ORGANISM: Homo sapiens

<400> SEQUENCE: 7

```
gaaattgtgt tgacgcagtc tccaggcacc ctgtctttgt ctccagggga aagagccacc      60
ctctcctgca gggccagtca gagtgttagc agcagctact tagcctggta ccagcagaag      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcacctcc gtacactttt      300
ggccagggga ccaagctgga gatcaaa                                          327
```

<210> SEQ ID NO 8
<211> LENGTH: 109
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

-continued

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Glu Ile Lys
                100                 105
```